US010646666B2

United States Patent
Cohn et al.

(10) Patent No.: US 10,646,666 B2
(45) Date of Patent: May 12, 2020

(54) CRYOLIPOLYSIS DEVICES AND METHODS THEREFOR

(71) Applicant: TVA Medical, Inc., Austin, TX (US)

(72) Inventors: William E. Cohn, Bellaire, TX (US); Thomas Diffley Pate, Austin, TX (US); Adam L. Berman, Austin, TX (US)

(73) Assignee: TVA Medical, Inc., Franklin Lakes, NJ (US)

( * ) Notice: Subject to any disclaimer, the term of this patent is extended or adjusted under 35 U.S.C. 154(b) by 542 days.

(21) Appl. No.: 14/838,225

(22) Filed: Aug. 27, 2015

(65) Prior Publication Data

US 2016/0058956 A1     Mar. 3, 2016

Related U.S. Application Data

(60) Provisional application No. 62/042,732, filed on Aug. 27, 2014.

(51) Int. Cl.
    *A61B 18/02*      (2006.01)
    *A61M 5/44*      (2006.01)
    (Continued)

(52) U.S. Cl.
    CPC ............... *A61M 5/44* (2013.01); *A61B 18/02* (2013.01); *A61M 5/14* (2013.01); *A61M 5/422* (2013.01);
    (Continued)

(58) Field of Classification Search
    CPC .......... A61M 5/14; A61M 5/422; A61M 5/44; A61B 18/02; A61B 2018/0262
    See application file for complete search history.

(56) References Cited

U.S. PATENT DOCUMENTS

| 3,649,850 A | 3/1972 | Davis |
| 3,827,436 A * | 8/1974 | Stumpf .................. A61B 18/02 606/23 |

(Continued)

FOREIGN PATENT DOCUMENTS

| CA | 2883209 A1 | 4/2014 |
| CN | 1730123 A | 2/2006 |

(Continued)

OTHER PUBLICATIONS

Banasik et al. (2011). "A rare variant route of the ulnar artery does not contraindicate the creation of a fistula in the wrist of a diabetic patient with end-stage renal disease," *Postepy Hig Med Dosw.* 65:654-657.

(Continued)

*Primary Examiner* — Daniel W Fowler
(74) *Attorney, Agent, or Firm* — Dinsmore & Shohl LLP

(57) ABSTRACT

Described herein are cryolipolysis devices, systems, and methods for facilitating percutaneous access to a target blood vessel by performing cryolipolysis on subcutaneous adipose tissue obscuring the target blood vessel (e.g., a vessel used for hemodialysis treatment). Generally, the devices include a cooling member carrying a coolant that cools a selected portion of adipose tissue overlying the target blood vessel to reduce the selected portion of adipose tissue, thereby forming a depression in the adipose tissue and allowing the target blood vessel closer to the surface of the skin. In some variations, the cooling member is placed subcutaneously to directly cool the selected portion of adipose tissue. In other variations, the cooling member is placed external to the patient to indirectly cool the selected portion of adipose tissue through the skin.

13 Claims, 21 Drawing Sheets

(51) Int. Cl.
*A61B 18/00* (2006.01)
*A61M 5/14* (2006.01)
*A61M 5/42* (2006.01)

(52) U.S. Cl.
CPC .............. *A61B 2018/00458* (2013.01); *A61B 2018/0212* (2013.01)

(56) References Cited

U.S. PATENT DOCUMENTS

| | | |
|---|---|---|
| 4,416,664 A | 11/1983 | Womack |
| 4,802,475 A * | 2/1989 | Weshahy ............ A61B 18/0218 128/DIG. 27 |
| 5,313,943 A | 5/1994 | Houser et al. |
| 5,697,909 A | 12/1997 | Eggers et al. |
| 5,800,487 A | 9/1998 | Mikus et al. |
| 5,830,222 A | 11/1998 | Makower |
| 5,830,224 A | 11/1998 | Cohn et al. |
| 5,895,404 A | 4/1999 | Ruiz |
| 5,971,979 A | 10/1999 | Joye et al. |
| 6,004,330 A | 12/1999 | Middleman et al. |
| 6,032,677 A | 3/2000 | Blechman et al. |
| 6,039,730 A * | 3/2000 | Rabin .................... A61B 18/02 606/21 |
| 6,068,638 A | 5/2000 | Makower |
| 6,099,542 A | 8/2000 | Cohn et al. |
| 6,159,225 A | 12/2000 | Makower |
| 6,190,353 B1 | 2/2001 | Makower et al. |
| 6,197,025 B1 | 3/2001 | Grossi et al. |
| 6,217,575 B1 | 4/2001 | DeVore et al. |
| 6,231,587 B1 | 5/2001 | Makower |
| 6,256,525 B1 | 7/2001 | Yang et al. |
| 6,283,988 B1 | 9/2001 | Laufer et al. |
| 6,287,306 B1 | 9/2001 | Kroll et al. |
| 6,302,875 B1 | 10/2001 | Makower et al. |
| 6,327,505 B1 | 12/2001 | Medhkour et al. |
| 6,347,247 B1 | 2/2002 | Dev et al. |
| 6,355,029 B1 | 3/2002 | Joye et al. |
| 6,357,447 B1 | 3/2002 | Swanson et al. |
| 6,379,353 B1 | 4/2002 | Nichols |
| 6,383,180 B1 | 5/2002 | LaLonde et al. |
| 6,400,976 B1 | 6/2002 | Champeau |
| 6,428,534 B1 | 8/2002 | Joye et al. |
| 6,461,356 B1 | 10/2002 | Patterson |
| 6,464,665 B1 | 10/2002 | Heuser |
| 6,464,723 B1 | 10/2002 | Callol |
| 6,468,268 B1 | 10/2002 | Abboud et al. |
| 6,475,214 B1 | 11/2002 | Moaddeb |
| 6,475,226 B1 | 11/2002 | Belef et al. |
| 6,527,724 B1 | 3/2003 | Fenici |
| 6,527,769 B2 | 3/2003 | Langberg et al. |
| 6,542,766 B2 | 4/2003 | Hall et al. |
| 6,544,230 B1 | 4/2003 | Flaherty et al. |
| 6,569,158 B1 | 5/2003 | Abboud et al. |
| 6,569,162 B2 | 5/2003 | He |
| 6,579,311 B1 | 6/2003 | Makower |
| 6,585,650 B1 | 7/2003 | Solem |
| 6,592,577 B2 | 7/2003 | Abboud et al. |
| 6,635,053 B1 | 10/2003 | LaLonde et al. |
| 6,655,386 B1 | 12/2003 | Makower et al. |
| 6,656,173 B1 | 12/2003 | Palermo |
| 6,663,625 B1 | 12/2003 | Ormsby et al. |
| 6,669,709 B1 | 12/2003 | Cohn et al. |
| 6,676,657 B2 | 1/2004 | Wood |
| 6,682,525 B2 | 1/2004 | LaLonde et al. |
| 6,695,878 B2 | 2/2004 | McGuckin, Jr. et al. |
| 6,709,444 B1 | 3/2004 | Makower |
| 6,719,756 B1 | 4/2004 | Muntermann |
| 6,726,697 B2 | 4/2004 | Nicholas et al. |
| 6,733,494 B2 | 5/2004 | Abboud et al. |
| 6,736,808 B1 | 5/2004 | Motamedi et al. |
| 6,761,708 B1 | 7/2004 | Chiu |
| 6,761,714 B2 | 7/2004 | Abboud et al. |
| 6,780,181 B2 | 8/2004 | Kroll et al. |
| 6,849,073 B2 | 2/2005 | Hoey et al. |
| 6,855,143 B2 | 2/2005 | Davison et al. |
| 6,887,234 B2 | 5/2005 | Abboud et al. |
| 6,911,026 B1 | 6/2005 | Hall et al. |
| 6,932,814 B2 | 8/2005 | Wood |
| 6,936,024 B1 | 8/2005 | Houser |
| 6,960,209 B2 | 11/2005 | Clague et al. |
| 6,971,983 B1 | 12/2005 | Cancio |
| 6,981,972 B1 | 1/2006 | Farley et al. |
| 7,059,330 B1 | 6/2006 | Makower et al. |
| 7,060,063 B2 | 6/2006 | Marion |
| 7,094,235 B2 | 8/2006 | Francischelli |
| 7,155,293 B2 | 12/2006 | Westlund et al. |
| 7,189,231 B2 | 3/2007 | Clague et al. |
| 7,214,234 B2 | 5/2007 | Rapacki et al. |
| 7,231,260 B2 | 6/2007 | Wallace et al. |
| 7,250,051 B2 | 7/2007 | Francischelli |
| 7,288,075 B2 | 10/2007 | Parihar et al. |
| 7,303,554 B2 | 12/2007 | LaLonde et al. |
| 7,306,598 B2 | 12/2007 | Truckai et al. |
| 7,335,198 B2 | 2/2008 | Eggers et al. |
| 7,341,063 B2 | 3/2008 | Garbibaldi et al. |
| 7,367,341 B2 * | 5/2008 | Anderson .............. A61B 5/415 128/898 |
| 7,374,567 B2 | 5/2008 | Heuser |
| 7,387,636 B2 | 6/2008 | Cohn et al. |
| 7,407,506 B2 | 8/2008 | Makower |
| 7,628,768 B2 | 12/2009 | Faul et al. |
| 7,702,387 B2 | 4/2010 | Stevenson et al. |
| 7,727,268 B2 | 6/2010 | Cunniffe et al. |
| 7,744,596 B2 | 6/2010 | Young et al. |
| 7,811,281 B1 | 10/2010 | Rentrop |
| 7,828,814 B2 | 11/2010 | Brenneman et al. |
| 7,846,172 B2 | 12/2010 | Makower |
| 7,849,860 B2 | 12/2010 | Makower et al. |
| 7,857,809 B2 | 12/2010 | Drysen |
| 7,881,797 B2 | 2/2011 | Griffin et al. |
| 7,955,326 B2 | 6/2011 | Paul et al. |
| 7,967,769 B2 | 6/2011 | Faul et al. |
| 7,967,770 B2 | 6/2011 | Li et al. |
| 8,010,208 B2 | 8/2011 | Nimer et al. |
| 8,048,016 B2 | 11/2011 | Faul et al. |
| 8,052,680 B2 | 11/2011 | Hassell et al. |
| 8,062,321 B2 | 11/2011 | Heuser et al. |
| RE43,007 E | 12/2011 | LaLonde et al. |
| 8,075,555 B2 | 12/2011 | Truckai et al. |
| 8,088,171 B2 | 1/2012 | Brenneman |
| 8,100,899 B2 | 1/2012 | Doty et al. |
| 8,118,809 B2 | 2/2012 | Paul et al. |
| 8,135,467 B2 | 3/2012 | Markowitz et al. |
| 8,142,454 B2 | 3/2012 | Harrison et al. |
| 8,192,425 B2 | 6/2012 | Mirza et al. |
| 8,200,466 B2 | 6/2012 | Spilker et al. |
| 8,226,592 B2 | 7/2012 | Brenneman et al. |
| 8,231,618 B2 | 7/2012 | Viswanathan et al. |
| 8,236,014 B2 | 8/2012 | Brenneman et al. |
| 8,262,649 B2 | 9/2012 | Francischelli |
| 8,273,095 B2 | 9/2012 | Brenneman et al. |
| 8,333,758 B2 | 12/2012 | Joye et al. |
| 8,361,061 B2 | 1/2013 | Esch et al. |
| 8,366,707 B2 | 2/2013 | Kassab et al. |
| 8,382,697 B2 | 2/2013 | Brenneman et al. |
| 8,409,196 B2 | 4/2013 | Durgin et al. |
| 8,413,664 B2 | 4/2013 | Appling |
| 8,414,572 B2 | 4/2013 | Davison et al. |
| 8,419,681 B2 | 4/2013 | Sell |
| 8,439,909 B2 | 5/2013 | Wang et al. |
| 8,454,587 B2 | 6/2013 | LaLonde et al. |
| 8,475,441 B2 | 7/2013 | Babkin et al. |
| 8,486,062 B2 | 7/2013 | Belhe et al. |
| 8,486,064 B2 | 7/2013 | Van Wyk et al. |
| 8,551,032 B2 | 10/2013 | Faul et al. |
| 8,574,185 B2 | 11/2013 | Faul et al. |
| 8,585,700 B2 | 11/2013 | Katou |
| 8,608,754 B2 | 12/2013 | Wensel et al. |
| 8,641,724 B2 | 2/2014 | Brenneman et al. |
| 8,649,879 B2 | 2/2014 | DiGiore et al. |
| 8,676,309 B2 | 3/2014 | Deem et al. |
| 8,685,014 B2 | 4/2014 | Babkin et al. |
| 8,700,179 B2 | 4/2014 | Pianca et al. |

(56) References Cited

U.S. PATENT DOCUMENTS

| | | |
|---|---|---|
| 8,715,281 B2 | 5/2014 | Barlow et al. |
| 8,758,334 B2 | 6/2014 | Coe et al. |
| 8,784,409 B2 | 6/2014 | Robilotto et al. |
| 8,771,267 B2 | 7/2014 | Kunis et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2 | 5/2015 | Miller et al. |
| 9,072,880 B2 | 7/2015 | Phillips et al. |
| 9,089,316 B2 | 7/2015 | Baust et al. |
| 9,155,827 B2 | 10/2015 | Franano |
| 9,204,916 B2 | 12/2015 | Lalonde |
| 9,283,034 B2 | 3/2016 | Katoh et al. |
| 9,364,280 B2 | 6/2016 | Zarins et al. |
| 9,402,560 B2 | 8/2016 | Organ et al. |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2 | 11/2016 | Rios et al. |
| 9,782,533 B2 | 10/2017 | Brenneman et al. |
| 2001/0029384 A1 | 10/2001 | Nicholas et al. |
| 2002/0072739 A1 | 6/2002 | Lee et al. |
| 2002/0113678 A1 | 8/2002 | Creighton |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0167506 A1 | 8/2004 | Chen |
| 2004/0215220 A1 | 10/2004 | Dolan et al. |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1* | 11/2005 | Anderson ............ A61B 5/6804 606/20 |
| 2006/0079897 A1 | 4/2006 | Harrison et al. |
| 2006/0111704 A1 | 5/2006 | Brenneman et al. |
| 2007/0173878 A1 | 7/2007 | Heuser |
| 2007/0203515 A1 | 8/2007 | Heuser et al. |
| 2008/0021532 A1 | 1/2008 | Kveen et al. |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1 | 5/2008 | Brenneman et al. |
| 2008/0140061 A1* | 6/2008 | Toubia ............... A61B 18/02 606/20 |
| 2008/0171944 A1 | 7/2008 | Brenneman et al. |
| 2008/0183164 A1* | 7/2008 | Elkins ............... A61B 18/02 606/21 |
| 2008/0188848 A1 | 8/2008 | Deutmeyer et al. |
| 2008/0275442 A1 | 11/2008 | Paul et al. |
| 2009/0036872 A1 | 2/2009 | Fitzgerald et al. |
| 2009/0076324 A1 | 3/2009 | Takayama et al. |
| 2009/0112119 A1 | 4/2009 | Kim |
| 2009/0118722 A1 | 5/2009 | Ebbers et al. |
| 2009/0124847 A1 | 5/2009 | Doty et al. |
| 2009/0198232 A1 | 8/2009 | Young et al. |
| 2009/0248148 A1 | 10/2009 | Shaolian et al. |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 | 4/2010 | Kassab |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Deitz et al. |
| 2010/0280514 A1 | 11/2010 | Zerfas et al. |
| 2010/0286705 A1 | 11/2010 | Vassiliades, Jr. |
| 2010/0292685 A1 | 11/2010 | Katoh et al. |
| 2010/0298645 A1 | 11/2010 | Deutch |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1 | 9/2011 | Kraemer et al. |
| 2011/0270149 A1 | 11/2011 | Faul et al. |
| 2011/0288392 A1 | 11/2011 | de la Rama et al. |
| 2011/0288544 A1 | 11/2011 | Verin et al. |
| 2011/0306959 A1 | 12/2011 | Kellerman et al. |
| 2011/0306993 A1 | 12/2011 | Hull et al. |
| 2011/0319976 A1 | 12/2011 | Iyer et al. |
| 2012/0010556 A1 | 1/2012 | Faul et al. |
| 2012/0022518 A1* | 1/2012 | Levinson ............ A61B 18/02 606/33 |
| 2012/0035539 A1 | 2/2012 | Tegg |
| 2012/0046678 A1 | 2/2012 | LeMaitre et al. |
| 2012/0059398 A1 | 3/2012 | Pate et al. |
| 2012/0065652 A1 | 3/2012 | Cully et al. |
| 2012/0078342 A1 | 3/2012 | Vollkron et al. |
| 2012/0089123 A1 | 4/2012 | Organ et al. |
| 2012/0101423 A1 | 4/2012 | Brenneman et al. |
| 2012/0116354 A1 | 5/2012 | Heuser |
| 2012/0157992 A1 | 6/2012 | Smith et al. |
| 2012/0209377 A1 | 8/2012 | Machold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |
| 2012/0302935 A1 | 11/2012 | Miller et al. |
| 2013/0041306 A1 | 2/2013 | Faul et al. |
| 2013/0056876 A1 | 5/2013 | Harvey et al. |
| 2013/0110105 A1 | 5/2013 | Vankov |
| 2013/0172881 A1 | 7/2013 | Hill et al. |
| 2013/0190744 A1 | 7/2013 | Avram et al. |
| 2013/0190754 A1 | 7/2013 | Paul et al. |
| 2013/0216351 A1 | 8/2013 | Griffin |
| 2013/0226170 A1 | 8/2013 | Seddon et al. |
| 2013/0261368 A1* | 10/2013 | Schwartz ............ A61N 5/1027 600/1 |
| 2013/0282000 A1 | 10/2013 | Parsonage |
| 2014/0031674 A1 | 1/2014 | Newman et al. |
| 2014/0094791 A1 | 4/2014 | Hull et al. |
| 2014/0100557 A1 | 4/2014 | Bohner et al. |
| 2014/0100562 A1 | 4/2014 | Sutermeister et al. |
| 2014/0107642 A1 | 4/2014 | Rios et al. |
| 2014/0166098 A1 | 6/2014 | Kian et al. |
| 2014/0188028 A1 | 7/2014 | Brenneman et al. |
| 2014/0276335 A1 | 9/2014 | Pate |
| 2015/0005759 A1 | 1/2015 | Welches et al. |
| 2015/0011909 A1 | 1/2015 | Holmin et al. |
| 2015/0018810 A1 | 1/2015 | Baust et al. |
| 2015/0057654 A1 | 2/2015 | Leung et al. |
| 2015/0057687 A1 | 2/2015 | Gittard et al. |
| 2015/0080886 A1 | 3/2015 | Miller et al. |
| 2015/0094645 A1 | 4/2015 | Omar-Pasha |
| 2015/0112195 A1 | 4/2015 | Berger et al. |
| 2015/0134055 A1 | 5/2015 | Spence et al. |
| 2015/0141836 A1 | 5/2015 | Naumann et al. |
| 2015/0164573 A1 | 6/2015 | Delaney |
| 2015/0196356 A1 | 7/2015 | Kauphusman et al. |
| 2015/0196360 A1 | 7/2015 | Grantham et al. |
| 2015/0201962 A1 | 7/2015 | Kellerman et al. |
| 2015/0258308 A1 | 9/2015 | Pate |
| 2015/0313668 A1 | 11/2015 | Miller et al. |
| 2015/0320472 A1 | 11/2015 | Ghaffari et al. |
| 2016/0022345 A1 | 1/2016 | Baust et al. |
| 2016/0058452 A1 | 3/2016 | Brenneman et al. |
| 2016/0058956 A1 | 3/2016 | Cohn et al. |
| 2016/0067449 A1 | 3/2016 | Misener et al. |
| 2016/0082234 A1 | 3/2016 | Schwartz et al. |
| 2016/0128855 A1 | 5/2016 | Heuser et al. |

(56) References Cited

U.S. PATENT DOCUMENTS

| | | | |
|---|---|---|---|
| 2016/0135881 A1 | 5/2016 | Katoh et al. |
| 2016/0184011 A1 | 6/2016 | Krishnan |
| 2017/0119464 A1 | 5/2017 | Rios et al. |
| 2017/0172679 A1 | 6/2017 | Doty et al. |
| 2017/0202603 A1 | 7/2017 | Cohn et al. |
| 2017/0202616 A1 | 7/2017 | Pate et al. |
| 2018/0116522 A1 | 5/2018 | Brenneman et al. |

FOREIGN PATENT DOCUMENTS

| | | |
|---|---|---|
| CN | 101730557 A | 6/2010 |
| EP | 0 889 705 A1 | 1/1999 |
| JP | H-11-512640 A | 11/1999 |
| JP | 2004-501720 A | 1/2004 |
| JP | 3493464 B2 | 2/2004 |
| RU | 2168951 C1 | 6/2001 |
| WO | WO-97/33522 A1 | 9/1997 |
| WO | WO-99/56640 A1 | 11/1999 |
| WO | WO-02/02163 A2 | 1/2002 |
| WO | WO-02/02163 A3 | 1/2002 |
| WO | 2008010039 A2 | 1/2008 |
| WO | WO-2009/005644 A2 | 1/2009 |
| WO | WO-2009/005644 A3 | 1/2009 |
| WO | WO-2011/100625 A2 | 8/2011 |
| WO | WO-2011/100625 A3 | 8/2011 |
| WO | WO-2012/068273 A1 | 5/2012 |
| WO | 2013112584 A1 | 8/2013 |
| WO | WO-2014/052919 A1 | 4/2014 |
| WO | WO-2014/059351 A1 | 4/2014 |
| WO | WO-2014/137830 A1 | 9/2014 |
| WO | WO-2014/153229 A1 | 9/2014 |
| WO | WO-2015/040557 A1 | 3/2015 |
| WO | WO-2015/061614 A1 | 4/2015 |
| WO | WO-2015/085119 A1 | 6/2015 |
| WO | 2015108984 A1 | 7/2015 |
| WO | WO-2016/033374 | 3/2016 |
| WO | WO-2016/033374 A1 | 3/2016 |
| WO | WO-2016/033380 A1 | 3/2016 |
| WO | WO-2017/124059 | 7/2017 |
| WO | WO-2017/124060 | 7/2017 |
| WO | WO-2017/124062 | 7/2017 |
| WO | 2018057095 A1 | 3/2018 |

OTHER PUBLICATIONS

Bharat et al. (2012). "A novel technique of vascular anastomosis to prevent juxta-anastomotic stenosis following arteriovenous fistula creation," *J. Vascular Surgery* 55(1):274-280.
Bode et al. (2011). "Clinical study protocol for the arch project Computational modeling for improvement of outcome after vascular access creation," *J. Vasc. Access* 12(4):369-376.
Davidson, I. et al. (2008). "Duplex Ultrasound Evaluation for Dialysis Access Selection and Maintenance: A Practical Guide," *The Journal of Vascular Access* 9(1):1-9.
Extended European Search Report dated Oct. 19, 2016, for EP Application No. 14 770 396.1, filed on Mar. 14, 2014, 7 pages.
Final Office Action dated Mar. 10, 2016, for U.S. Appl. No. 14/052,477, filed Oct. 11, 2013, 11 pages.
Final Office Action dated Oct. 6, 2016, for U.S. Appl. No. 14/697,451, filed Apr. 27, 2015, 11 pages.
Gracz, et al. (1977). "Proximal forearm fistula for maintenance hemodialysis," *Kidney International* 11:71-75.
International Search Report and Written Opinion dated Feb. 23, 2012, for PCT Patent Application No. PCT/US2011/061026, filed on Nov. 16, 2011, 8 pages.
International Search Report and Written Opinion dated Jan. 10, 2014, for PCT Patent Application No. PCT/US2013/064657, filed on Oct. 11, 2013, 8 pages.
International Search Report and Written Opinion dated Aug. 22, 2014, for PCT Patent Application No. PCT/US2014/029731, filed on Mar. 14, 2014, 11 pages.

International Search Report and Written Opinion dated Jun. 17, 2015, for PCT Patent Application No. PCT/US2015/020604, filed on Mar. 13, 2015, 8 pages.
Jennings, W.C. et al. (2011). "Primary arteriovenous fistula inflow proximalization for patients at high risk for dialysis access-associated ischemic steal syndrome," *J. Vasc. Surgery* 54(2):554-558.
Kinnaert, et al. (1971). "Ulnar Arteriovenous Fistula for Maintenance Haemodialysis," *British J. Surgery* 58(9):641-643.
Morale et al. (2011). "Venae comitantes as a potential vascular resource to create native arteriovenous fistulae," *J. Vasc. Access* 12(3):211-214.
Non-Final Office Action dated May 2, 2016, for U.S. Appl. No. 14/697,451, filed Apr. 27, 2015, 12 pages.
Non-Final Office Action dated Aug. 8, 2014, for U.S. Appl. No. 13/298,169, filed Nov. 16, 2011, 15 pages.
Non-Final Office Action dated Jul. 29, 2015, for U.S. Appl. No. 14/052,477, filed Oct. 11, 2013, 15 pages.
Notice of Allowance dated Dec. 31, 2014, for U.S. Appl. No. 13/298,169, filed Nov. 16, 2011, 10 pages.
Notice of Allowance dated Mar. 11, 2015, for U.S. Appl. No. 13/298,169, filed Nov. 16, 2011, 4 pages.
Notice of Allowance dated Jan. 23, 2015, for U.S. Appl. No. 14/550,747, filed Nov. 21, 2014, 10 pages.
Notice of Allowance dated Jul. 12, 2016, for U.S. Appl. No. 14/052,477, filed Oct. 11, 2013, 7 pages.
Shenoy, S. (2009). "Surgical anatomy of upper arm: what is needed for AVF planning," *The Journal of Vascular Access* 10:223-232.
Vachharajani, T. (2010). "Atlas of Dialysis Vascular Access," Wake Forest University School of Medicine, 77 total pages.
Whittaker et al. (2011). "Prevention better than cure. Avoiding steal syndrome with proximal radial or ulnar arteriovenous fistulae," *J. Vasc. Access* 12(4):318-320.
International Search Report and Written Opinion dated Mar. 31, 2017, for PCT Patent Application No. PCT/US17/13611, filed on Jan. 15, 2017, 10 pages.
Non-Final Office Action dated Apr. 13, 2017, for U.S. Appl. No. 14/697,451, filed Apr. 27, 2015, 19 pages.
Invitation to Pay Additional Fees and, Where Applicable, Protest Fee dated Mar. 31, 2017, for PCT Application No. PCT/US17/13613, filed Jan. 15, 2017, 3 pages.
International Search Report and Written Opinion dated Jun. 1, 2017, for PCT Patent Application No. PCT/US2017/13613, filed Jan. 15, 2017, 18 pages.
Non-Final Office Action dated Jul. 10, 2017, for U.S. Appl. No. 14/214,503, filed Mar. 14, 2014, 11 pages.
Final Office Action dated Aug. 29, 2017, for U.S. Appl. No. 14/697,451, filed Apr. 27, 2015, 16 pages.
International Search Report and Written Opinion dated Sep. 28, 2017, by the International Searching Authority for Application No. PCT/US2017/042937, filed Jul. 19, 2017, 11, pages.
Extended European Search Report dated Oct. 16, 2017, for EP Application No. 11841243.6, filed Nov. 16, 2011, 6 pages.
Non-Final Office Action issued by the United States Patent and Trademark Office for U.S. Appl. No. 14/657,997, dated Oct. 18, 2017, 10 pages.
International Search Report Written Opinion issued by the International Searching Authority for Application No. PCTUS2015047274, filed Aug. 27, 2017, dated Jan. 6, 2016, 4 pages.
Written Opinion issued by the International Searching Authority for Application No. PCTUS2015047274, filed Aug. 27, 2017, dated Jan. 6, 2016, 8 pages.
Invitation to Pay Additional Fees and, Where Applicable, Protest Fee issued by the International Searching Authority for Application No. PCTUS2015047274, filed Aug. 27, 2017, dated Oct. 22, 2015, 2 pages.
Extended European Search Report for EP Application No. 17739123.2.
Choi, et al., Design of a Halbach Magnet Array Based on Optimization Techniques; IEEE Transactions on Magnetics, vol. 44, No. 10, Oct. 2008, pp. 2361-2366. (Year: 2008).

(56) References Cited

OTHER PUBLICATIONS

Maybury, et al., "The Effect of Roll Angle on the Performance of Halbach Arrays," University of California-San Diego, Center for Magnetic Recording Research (2008), 19 pgs.

Hakim et al., "Ulnar artery-based free forearm flap: Review of Specific anatomic features in 322 cases and related literature," Heand & Neck, Dec. 2013 (published online:2014), Wiley Online Library.

* cited by examiner

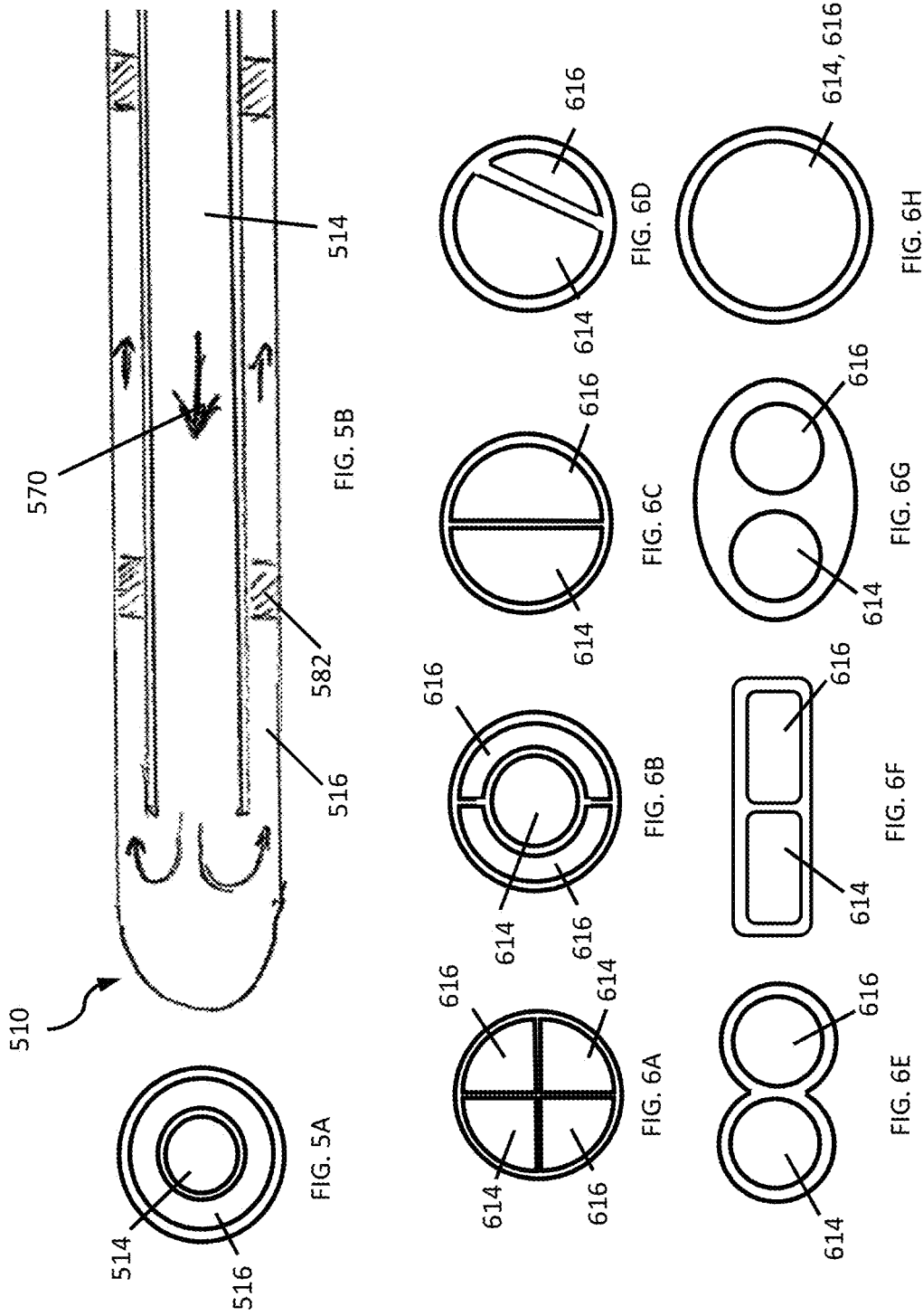

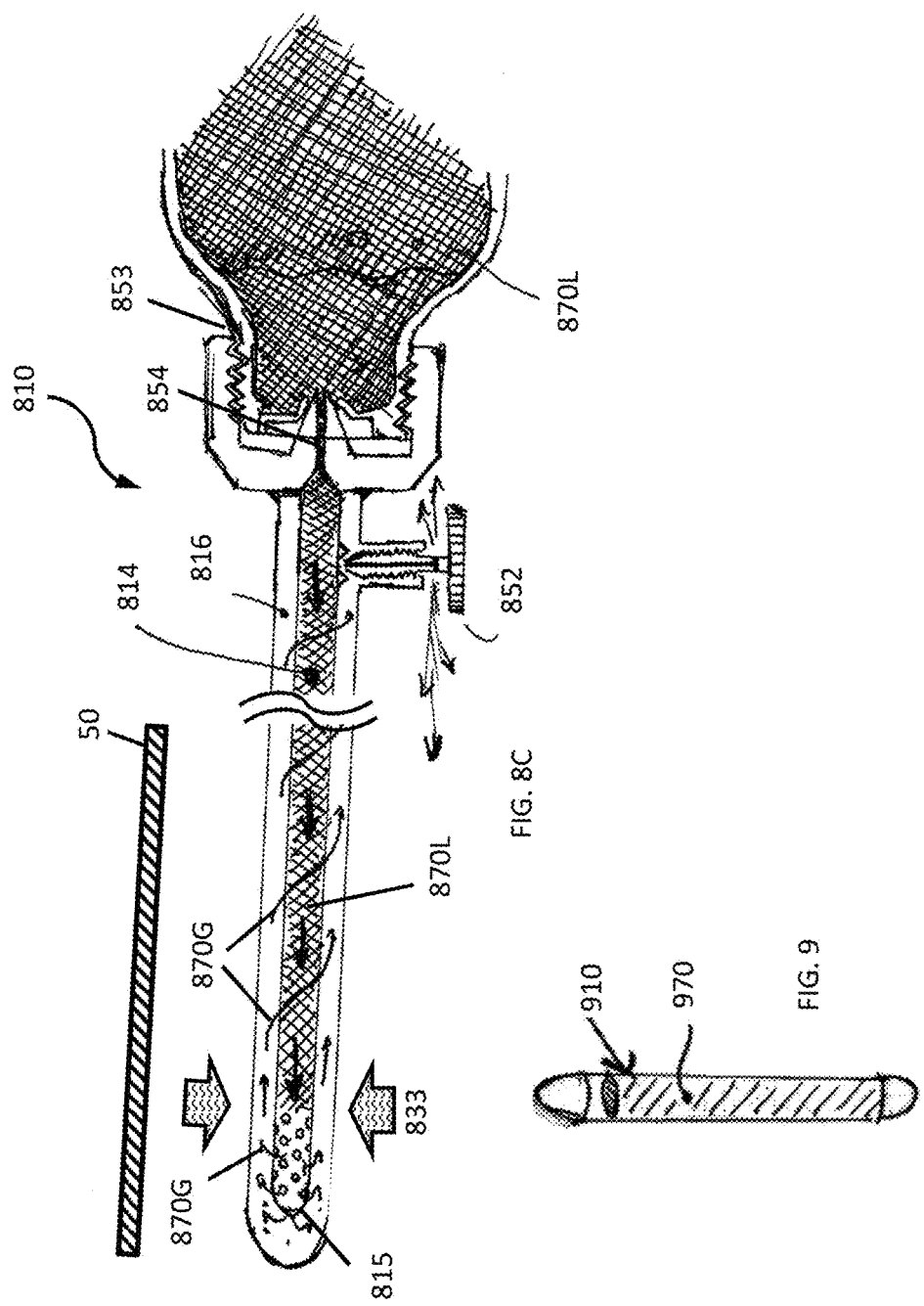

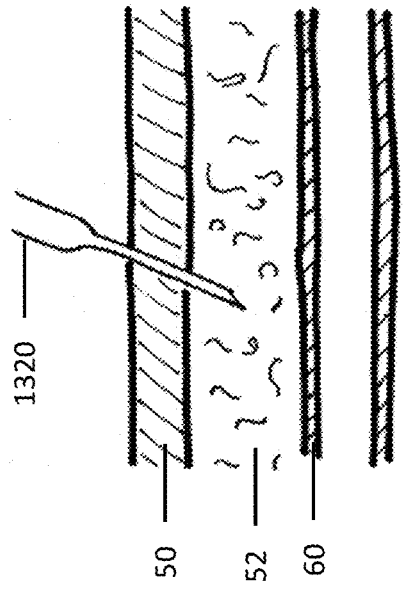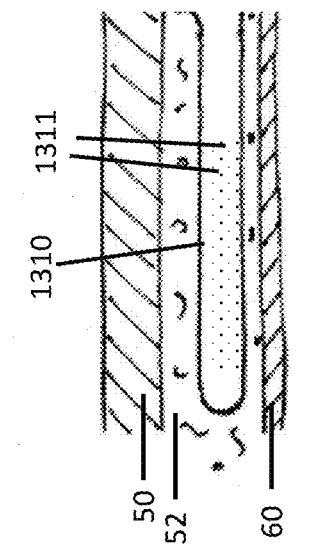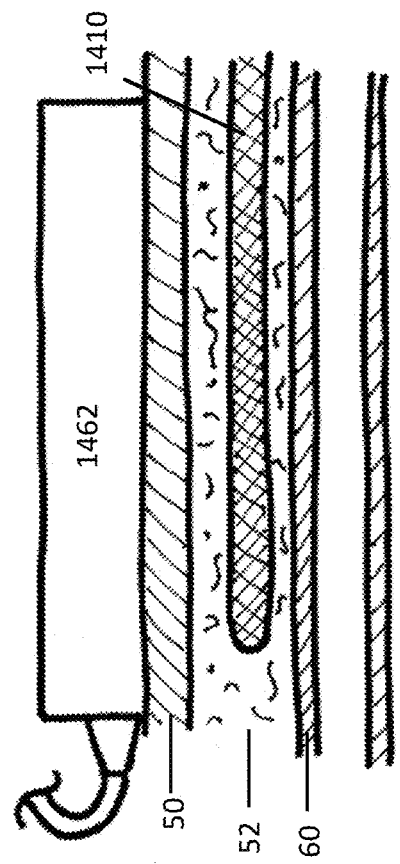

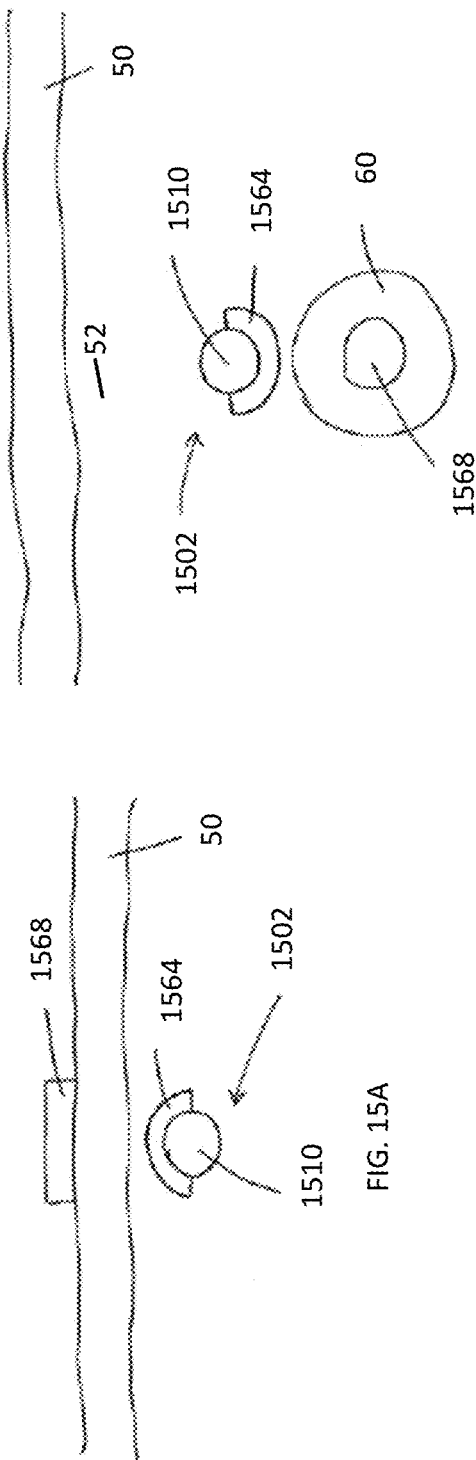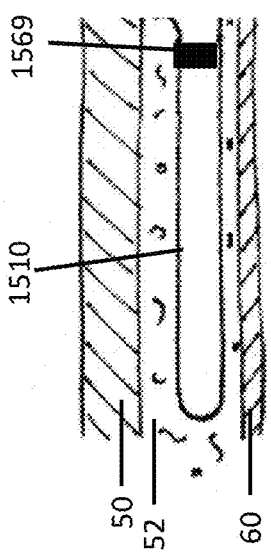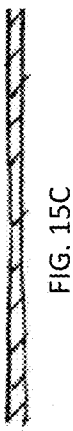

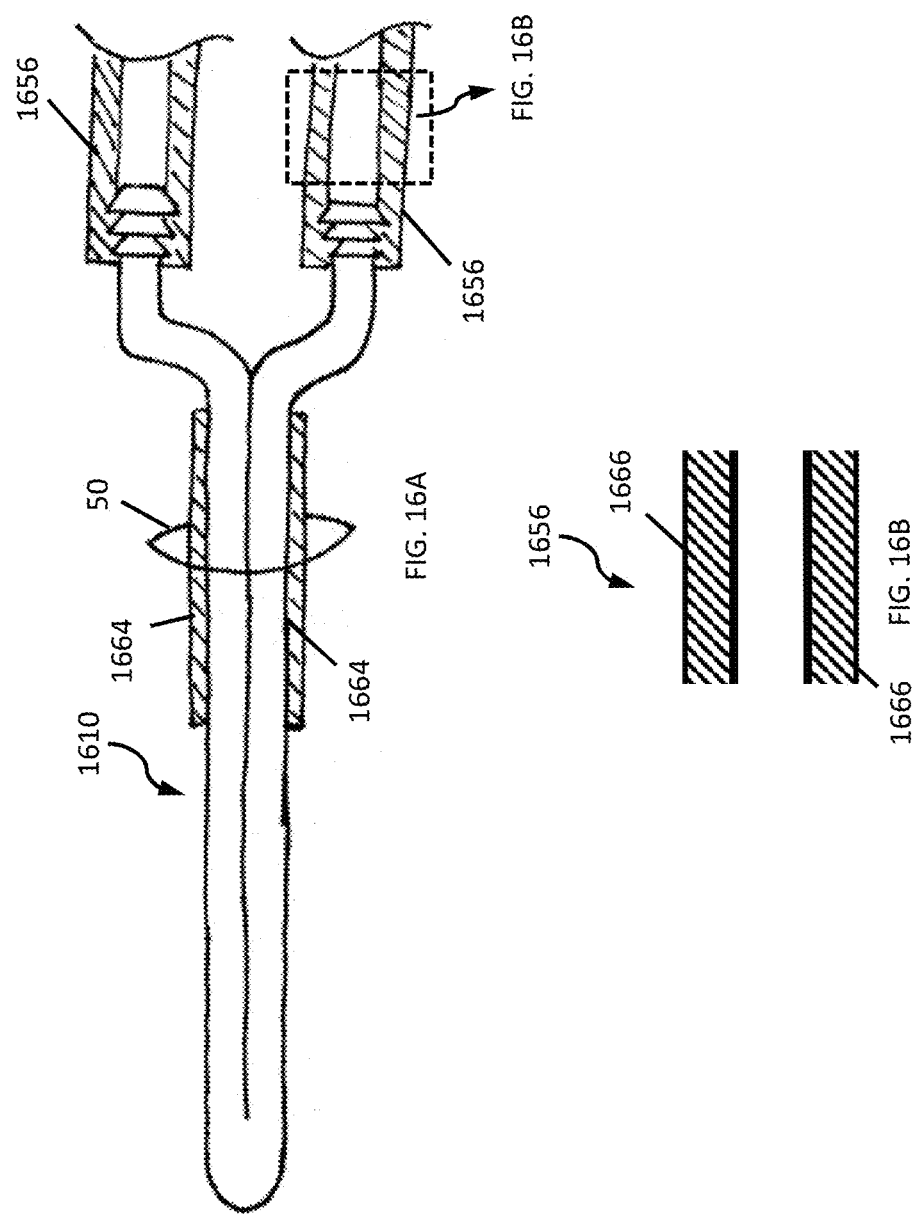

CRYOLIPOLYSIS DEVICES AND METHODS THEREFOR

CROSS-REFERENCE TO RELATED APPLICATIONS

This application claims priority to U.S. Provisional Application Ser. No. 62/042,732, filed on Aug. 27, 2014, and titled "CRYOLIPOLYSIS DEVICES AND METHODS THEREFOR," the content of which is hereby incorporated by reference in its entirety.

FIELD

The current invention relates to devices, systems, and methods for facilitating percutaneous access to blood vessels.

BACKGROUND

Hemodialysis treatment involves obtaining access to blood through one or more blood vessels. Specifically, one or more needles or catheters may be inserted into one or more blood vessels to draw or retrieve fluid. Preferably, the one or more vessels may be located close to the surface of the skin. Frequently, a fistula may be formed between two vessels to provide better access. A fistula allows blood to flow quickly between the vessels, while bypassing the capillaries. The quality of the vascular access that may be achieved may impact the adequacy of hemodialysis.

Typically, a vessel for vascular access (e.g., for hemodialysis) is ideally located about 5 mm or less from the skin of the patient. However, some vessels may be too deep below the skin and an underlying layer of fat to reach with a conventional needle. In some cases, it may be desirable to use one or more deep vessels whose access is obscured by a thicker layer of subcutaneous fat. As such, it may be desirable to have devices, systems, and methods to facilitate percutaneous access to these deep vessels.

BRIEF SUMMARY

Described herein are devices, systems, and methods for facilitating percutaneous access to blood vessels. In general, devices for facilitating percutaneous access to a target blood vessel in a patient comprises a subcutaneous probe to carry a coolant. The probe may comprise an adipose tissue interface surface and a treatment segment. The treatment segment may define a delivery lumen extending at least the length of the treatment segment to carry the coolant toward a distal end of the treatment segment and a return lumen to carry the coolant away from the distal end of the treatment segment.

In some variations, the treatment segment overlies and is substantially aligned with a treatment portion of the target blood vessel. In another variation, the delivery lumen and the return lumen may be in fluid communication with one another at the distal end of the treatment segment. The distal end of the treatment segment may be blunt. At least a portion of the delivery lumen and at least a portion of the return lumen may be separated by a porous wall. The probe may further comprise a valve coupled to the return lumen to control a rate of a phase transformation of the coolant across the porous wall.

In yet another variation, the delivery lumen and the return lumen may be substantially parallel. The delivery lumen may be annular and surround the return lumen. The return lumen may be annular and surround the delivery lumen. The delivery lumen and the return lumen may be laterally offset from one another. In some variations, at least one of the delivery lumen and the return lumen is approximately semi-circular.

The device may include additional variations. The probe may comprise a proximal probe portion directed along a first axis, and the treatment segment may be directed along a second axis that is oriented at a nonzero angle to the first axis. The adipose tissue interface surface may define at least one fenestration. A temperature sensor may be coupled to the treatment segment of the probe that measures at least one of the temperature of the treatment segment and the temperature of the coolant. The temperature sensor may be coupled to the distal end of the treatment segment.

The probe may further comprise an adipose tissue agitator. An insulator may be coupled to the probe. The insulator may be coupled to a transcutaneous segment of the probe. The insulator may be coupled to at least a portion of the treatment segment of the probe. In some particular variations, the probe may have an outer diameter of between approximately 5 millimeters and 8 millimeters.

Also described here are systems for facilitating percutaneous access to a target blood vessel in a patient. In general, these systems comprise a cooling device comprising a subcutaneous probe with an adipose tissue interface surface and a treatment segment defining a fluidic channel to carry a coolant. A cooling subsystem may be provided and comprises a cooling mechanism and a fluid distributor. The cooling mechanism modifies the temperature of the coolant, and the fluid distributor delivers coolant from the cooling mechanism at a flow rate into the fluidic channel of the probe.

These systems may include additional variations. The cooling mechanism may comprise a closed fluidic system with a heat exchanger. The cooling mechanism may comprise a coolant reservoir in fluid communication with the fluidic channel. The fluid distributor may comprise a pump. The fluid distributor may comprise a wick.

In some variations, a control subsystem may be coupled to the cooling subsystem to control at least one of the flow rate and the temperature of the coolant. The probe may include a temperature sensor that measures at least one of a temperature of the treatment segment of the probe and the temperature of the coolant. The temperature sensor may be located on the treatment segment.

In other variations, a guide member is provided to reposition the probe relative to a treatment portion of the target blood vessel. Each of the probe and the guide member may comprise a magnet. In yet another variation, the system may comprise an adipose tissue agitator. The adipose tissue agitator may agitate adipose tissue from a location external to the patient. The adipose tissue agitator may be coupled to the probe.

In yet further variations, the cooling device may comprise a sealing member detachable to a proximal portion of the subcutaneous probe. The coolant may be a pressurized liquid coolant, and the fluid distributor may inject the liquid coolant into the subcutaneous probe. A proximal portion of the subcutaneous probe may be open-ended. The liquid coolant may undergo a phase change and vent a vapor coolant from the proximal portion of the subcutaneous probe. The fluid distributor may comprise a coolant injector inserted into the subcutaneous probe to deliver the coolant to the fluidic channel.

Also described here are devices for facilitating percutaneous access to a target blood vessel in a patient. In general, these devices comprise a cooling member comprising a fluidic channel to carry a coolant. The fluidic channel comprises a treatment segment to cool a selected portion of adipose tissue. A securing member may couple the cooling member to an external surface of the patient such that the treatment segment of the fluidic channel overlies and is substantially aligned with a treatment portion of the target blood vessel.

In some variations of the devices, the fluidic channel may comprise tubing. A second cooling member may be provided and comprise a second fluidic channel. The securing member may comprise a cuff. The cooling member may be repositionable relative to the securing member. The cooling member may comprise a sealing member detachable to a proximal portion of the cooling member.

In other variations, a tissue gatherer may be coupled to the cooling member. The tissue gatherer may define a concave shape to hold tissue. The cooling member may be provided on an inner tissue interface surface of the tissue gatherer. At least one wire may actuate the tissue gatherer. A vacuum source may be coupled to the tissue gatherer.

Also described here are systems for facilitating percutaneous access to a target blood vessel in a patient generally comprising a cooling device comprising a cooling member comprising an elongate fluidic channel with a treatment segment to carry a coolant. A securing member may couple the cooling member to the skin of the patient such that the treatment segment of the fluidic channel overlies and is substantially aligned with a treatment portion of the target blood vessel. A cooling subsystem may comprise a cooling mechanism and a pump. The cooling mechanism may modify the temperature of the coolant. The pump may receive coolant from the cooling mechanism and deliver coolant at a flow rate into the fluidic channel of the cooling member. A control subsystem may be coupled to the cooling subsystem to control at least one of the flow rate and the temperature of the coolant. In some of these variations, the cooling mechanism may comprise a closed fluidic system with a heat exchanger. The cooling mechanism may comprise a coolant reservoir in fluidic communication with the fluidic channel.

Also described here are methods of facilitating percutaneous access to a target blood vessel in a patient. In general, these methods comprise inserting a subcutaneous probe into adipose tissue. The probe is aligned with a treatment portion of the target blood vessel. A selected portion of adipose tissue surrounding the probe is cooled, thereby forming a depression in the selected portion of adipose tissue overlying the treatment portion of the target blood vessel. In other variations, probe insertion comprises inserting a distal end of the probe into the adipose tissue at a first location proximate the treatment portion of the target blood vessel. Inserting the probe may further comprise passing the distal end of the probe out of the adipose tissue at a second location different from the first location.

In some variations of these methods, cooling the selected portion of adipose tissue comprises circulating a coolant in the probe. Circulating the coolant in the probe may comprise inducing turbulent flow of the coolant. Circulating the coolant in the probe may comprise inducing laminar flow of the coolant. Circulating the coolant in the probe may comprise introducing a liquid coolant into a delivery lumen of the probe. A temperature of the probe may be measured and at least one of a flow rate and a temperature of the coolant may be modulated based on the measured temperature of the probe.

In further variations, circulating the coolant in the probe may comprise allowing the coolant to absorb heat from the selected portion of the adipose tissue and vaporize from a liquid coolant into a gaseous coolant. Circulating the coolant in the probe may comprise allowing the gaseous coolant to enter a return lumen of the probe. Circulating the coolant in the probe may comprise releasing the gaseous coolant from the probe and controlling a rate of release of the gaseous coolant, thereby controlling the rate at which the liquid coolant absorbs heat from the selected portion of the adipose tissue. Circulating the coolant in the probe may comprise condensing the gaseous coolant from the return lumen into the liquid coolant. Cooling the selected portion of the adipose tissue may comprise providing a solid or semi-solid coolant into the probe and allowing the solid or semi-solid coolant to undergo a phase transformation into a liquid or gas upon absorbing heat from the selected portion of the adipose tissue.

In other variations of the methods, the adipose tissue may be hydrodissected. Hydrodissecting adipose tissue may comprise introducing a fluid into the adipose tissue. Introducing the fluid may comprise injecting the fluid percutaneously. Introducing the fluid may comprise introducing the fluid through the probe.

In yet other variations of the methods described, vasculature in a skin of the patient overlying the selected portion of the adipose tissue is vasoconstricted. Vasoconstricting vasculature may comprises applying cold therapy to the skin of the patient overlying the selected portion of the adipose tissue. Vasoconstricting vasculature may comprise applying a vasoconstricting substance to the skin of the patient overlying the selected portion of the adipose tissue. Vasoconstricting vasculature may comprise applying positive pressure to the skin of the patient overlying the selected portion of the adipose tissue. Vasconstricting vasculature may comprise applying negative pressure to the skin of the patient overlying the selected portion of the adipose tissue.

The methods may include additional variations. The adipose tissue may be agitated. Agitating the adipose tissue may comprise applying vibration to the adipose tissue with a mechanical vibration source external to the patient. Agitating the adipose tissue comprises applying vibration to the adipose tissue with a mechanical vibration source internal to the patient. Applying vibration to the adipose tissue with the mechanical vibration source internal to the patient may comprise vibrating the probe. Agitating the adipose tissue may comprise applying acoustic vibration to the adipose tissue.

In yet further variations, cooling the selected portion of the adipose tissue comprises allowing dermis of the patient overlying the depression to lie within approximately 5 millimeters from the treatment portion of the target blood vessel. Cooling the selected portion of the adipose tissue may be performed repeatedly during a treatment period comprising at least seven days. Cooling the selected portion of the adipose tissue comprises forming a depression that is between approximately 10 millimeters and 40 millimeters deep. Cooling the selected portion of the adipose tissue comprises forming a depression that is between approximately 80 millimeters and 120 millimeters long. The target blood vessel may be at least one of the basilic vein and the cephalic vein. Coolant provided within the subcutaneous probe may be exchanged with another coolant.

Some variations of these methods may comprise sealing a proximal portion of the subcutaneous probe with a sealing member. The coolant may be injected in the subcutaneous probe continuously or periodically. The coolant having undergone a phase change from the probe may be removed.

Also described here are methods of facilitating percutaneous access to a target blood vessel in a patient, generally comprising providing a cooling member comprising a fluidic channel. The fluidic channel may be aligned with a treatment portion of the target blood vessel. The cooling member may be coupled to an external surface of the patient. A selected portion of adipose tissue overlying the treatment portion of the target blood vessel may be cooled, thereby forming a depression in the selected portion of the adipose tissue. In some variations, cooling the selected portion of the adipose tissue may comprise circulating a coolant in the probe. A temperature of the probe may be measured and at least one of a flow rate and a temperature of the coolant may be modulated based on the measured temperature of the probe.

Some variations of these methods may comprise hydrodissecting the adipose tissue. The adipose tissue may be agitated. Vasculature of the skin of the patient overlying the selected portion of adipose tissue may be vasoconstricted. Cooling the selected portion of the adipose tissue may comprise allowing dermis of the patient overlying the depression to lie within approximately 5 millimeters from the treatment portion of the target blood vessel.

In yet other variations, a second fluidic channel may be provided. The second fluidic channel may be aligned to a treatment portion of a second target blood vessel. A second selected portion of the adipose tissue overlying the treatment portion of the second target blood vessel may be cooled, thereby forming a second depression in the second selected portion of the adipose tissue. In another variation, the target blood vessel may comprise at least one of the basilic vein and the cephalic vein.

Further described here are methods of facilitating percutaneous access to a target blood vessel in a patient, generally comprising positioning a cooling member proximate to adipose tissue. The cooling member is aligned with a treatment portion of the target blood vessel. Cryolipolysis is performed on a selected portion of the adipose tissue adjacent the cooling member, thereby forming a depression in the selected portion of the adipose tissue overlying the treatment portion of the target blood vessel.

In other variations of the methods described, cooling the selected portion of the adipose tissue may comprise circulating a coolant into the cooling member. A temperature of the cooling member may be measured and at least one of a flow rate and a temperature of the coolant is modulated based on the measured temperature of the cooling member. Positioning the cooling member may comprise inserting a subcutaneous probe into the selected portion of the adipose tissue. In another variation, positioning the cooling member may comprise coupling a fluidic channel to an external surface of that patient overlying the selected portion of the adipose tissue.

Also described here are methods of facilitating percutaneous access to a target blood vessel in a patient, generally comprising forming a fistula in an arm of the patient. A subcutaneous probe may be inserted into adipose tissue overlying the target vein. The probe may be aligned with a treatment portion of the target vein. A selected portion of adipose tissue surrounding the probe may be cooled, thereby forming a depression in the selected portion of adipose tissue overlying the treatment portion of the target vein.

In some variations of these methods, the fistula may be a brachio-basilic fistula. The target vein may be a basilic vein. The arm may be dissected to provide access to the adipose tissue overlying the target vein. The alignment of the inserted subcutaneous probe may be verified by one of fluoroscopy and ultrasound. One of local anesthesia, general anesthesia or a brachial plexus block may be applied prior to forming the fistula. Hemodialysis treatment may be performed using the target vein. The probe may comprise a length of at least 8 mm, a diameter of 5 mm and a blunt distal portion. The probe may be inserted at a depth of 8 mm through a skin of the patient for the adipose tissue of 16 mm thickness. Cooling may be performed for 30 minutes at a temperature of 30° F.

BRIEF DESCRIPTION OF THE DRAWINGS

FIG. 5A depict another variation of an internal cooling device. FIG. 5B is a cross-sectional view of the device in FIG. 5A.

FIGS. 6A-6H depict cross-sectional views of delivery and return lumens of variations of an internal cooling device.

FIGS. 8A-8C and 9 depict additional variations of an internal cooling device with coolant that undergoes phase change. FIG. 8B is a cross-sectional view taken along line B-B of the device in FIG. 8A.

FIGS. 13A and 13B depict variations of hydrodissectors for hydrodissecting adipose tissue.

FIG. 14 depicts a variation of an adipose tissue agitator for agitating adipose tissue.

FIGS. 15A and 15B depict variations of guide members. FIG. 15C depicts a variation of imaging markers.

FIGS. 16A and 16B depict variations of insulation for use with the devices described herein.

DETAILED DESCRIPTION

Figure 1:
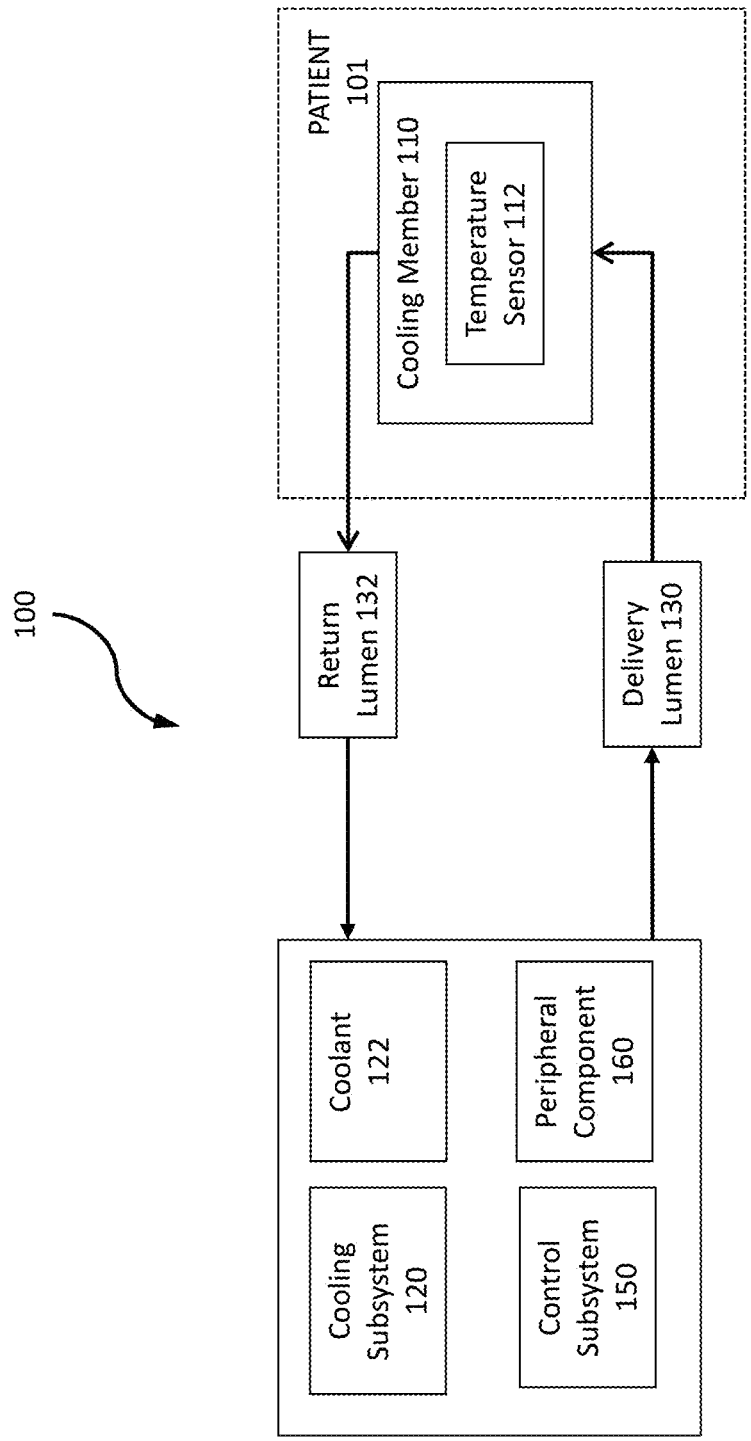
FIG. 1 is an illustrative block diagram of a system for facilitating percutaneous access to blood vessels.

Generally described here are devices, systems and methods for facilitating access to blood vessels, such as vessels for use in hemodialysis treatment. More particularly, described herein are devices, systems, and methods for facilitating percutaneous access to vessels that are obscured by a layer of subcutaneous fat. In some variations, the devices, systems, and methods described herein may improve access to fistulas formed using vessels having a deeper anatomical location than target sites for conventional surgical fistula-forming techniques (e.g., they may improve access to fistulas formed between an ulnar artery and a deep ulnar vein, using the methods described in U.S. patent application Ser. No. 14/052,477, filed Oct. 11, 2013, and titled "Devices and Methods for Fistula Formation," the entirety of which is hereby incorporated by reference).

Additionally or alternatively, the devices, systems, and methods described herein may improve access at other fistula sites, such as traditionally desirable target sites for conventional surgical fistula-forming techniques (e.g., radial artery-radial vein fistulas, certain fistulas in the legs). Access may be facilitated using a form of cryolipolysis. Generally speaking, cryolipolysis involves cooling of tissue to preferentially induce cell death of fat cells. When tissue is cooled, certain cells (e.g., skin cells) may be less sensitive to cold, and thus may remain intact following this exposure to cold, while fat cells may undergo localized cell death when cooled to the same temperatures, which may ultimately lead to reduction of the fatty tissue layer. As a result of extended and/or repeated exposure to cold, the reduction of fat between the skin and blood vessels may increase percutaneous access to the blood vessels.

Devices

Devices for facilitating percutaneous access to a target blood vessel include a cooling member that is placed proximate to a treatment portion of the target blood vessel to be used for vascular access (e.g., a portion of the basilic vein or cephalic vein to be used for hemodialysis). The cooling member cools a selected portion of adipose tissue overlying the treatment portion of the target blood vessel. This cooling may cause a reduction in volume of adipose tissue between the treatment portion of the target blood vessel and the skin of the patient. This may form a depression in the adipose tissue. As such, the surface of the skin may be able to lie closer to the treatment portion of the target blood vessel, improving percutaneous access to the treatment portion of the target blood vessel. As further described below, in some variations, the cooling member is subcutaneous and is placed internal to the patient in direct contact with adipose tissue. In other variations, the cooling member is external and placed over the skin of the patient to indirectly cool a selected portion of adipose tissue through the skin. In yet other variations, the devices may include any suitable combination of internal and external cooling members.

Some variations of the device include just the internal or external cooling member, while other variations of the device include an internal and/or external cooling member coupled to one or more additional elements. For example, in some variations, a cooling subsystem is coupled to the cooling member via delivery and return lumens to maintain a desired temperature of the cooling member using recirculating coolant. In other variations, a control subsystem may be further coupled to the cooling subsystem to control the flow rate and/or temperature of the coolant. In yet further variations, additional components such as an insulator, securing member vasoconstrictor, hydrodissector, tissue agitator and tissue gatherer may be coupled to the cooling member to further aid in improving patient outcomes.

As shown in the block diagram of FIG. 1, in some variations, a cooling device 100 for facilitating percutaneous access to a target blood vessel in a patient 101 includes a cooling member 110 placed proximate to a treatment portion of a target blood vessel of a patient 101, either external to the skin or subcutaneously. The cooling member 110 may be coupled to a cooling subsystem 120 via a delivery lumen 130 and a return lumen 132. The cooling subsystem 100 may include a coolant 122 for maintaining a desired temperature of the cooling member 110. The cooling subsystem 120 may control the rate and type of flow of the coolant 122 through the lumens 130/132 and cooling member 110 via a control subsystem 150 that receives one or more temperature measurements from a temperature sensor 112. In certain variations, the cooling device 100 includes only a subset of the components illustrated in FIG. 1. For example, the cooling device 100 may include just cooling member 110, coolant 122 and temperature sensor 112, and not include cooling subsystem 120, control subsystem 150, delivery and return lumens 130, 132 and so forth.

Internal Cooling Devices

Figure 2:
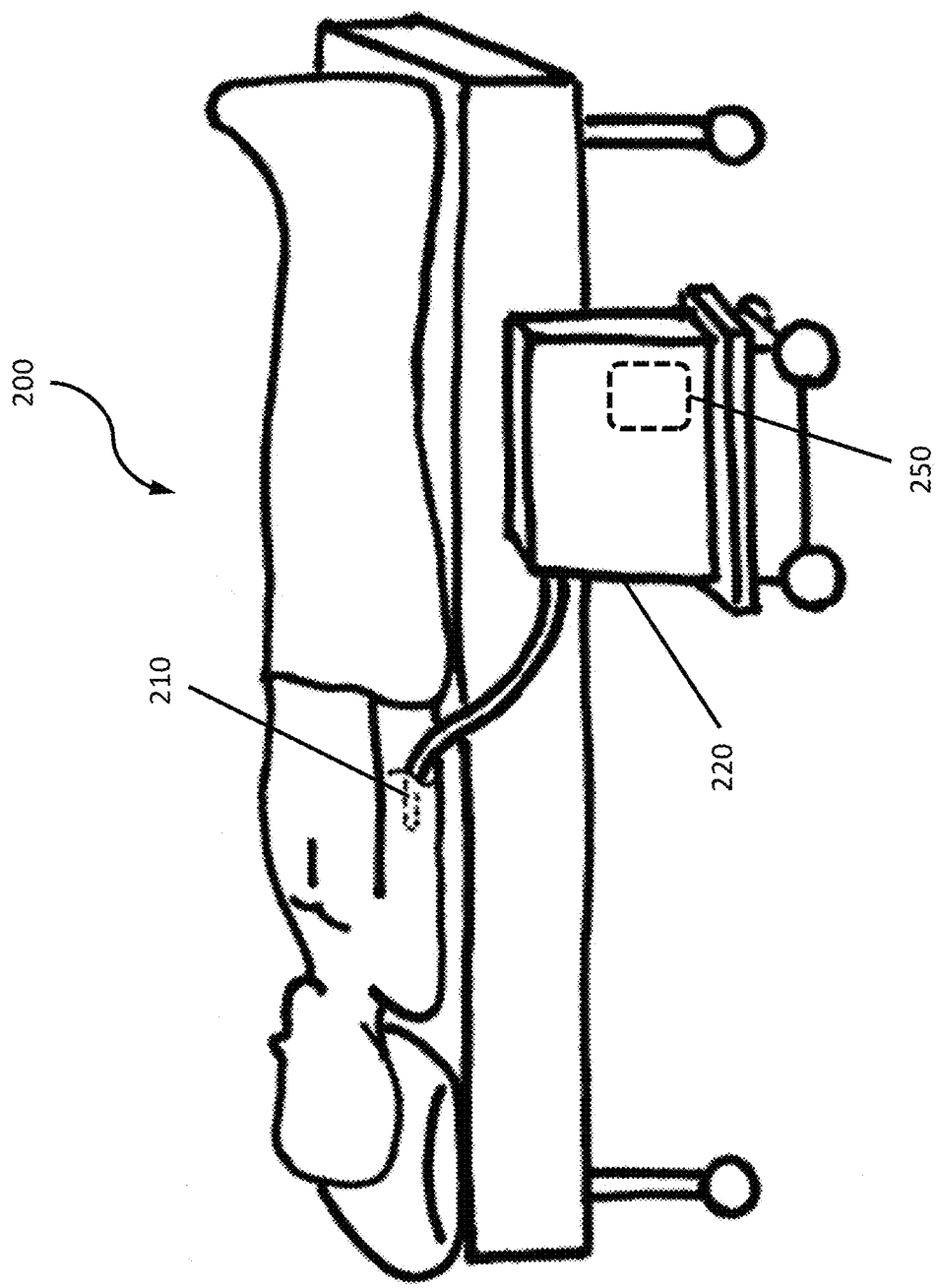
FIG. 2 depicts one variation of a system for facilitating percutaneous access to blood vessels with an internal cooling device.

As shown in FIG. 2, in some variations, an internal cooling device for facilitating percutaneous access to a target blood vessel in a patient includes a subcutaneous probe 210 that carries a coolant. In some variations, as described further below, the coolant is a fluid such as a liquid or gas, but in other variations, the coolant may be a solid or a semi-solid, such as a gel. The probe may be inserted subcutaneously to cool the adipose tissue between the target blood vessel and the skin of the patient. The probe may include an adipose tissue interface surface and a treatment segment for cooling a selected portion of adipose tissue. In some variations, the internal cooling device may be part of a system 200 that further includes a cooling subsystem 220 with a cooling mechanism that modifies the temperature of the coolant and a fluid distributor that receives coolant from the cooling mechanism and delivers coolant to the probe. In some variations, the system may further include a control subsystem 250 that controls the flow rate and/or temperature of the coolant.

Probe

Figure 3A:
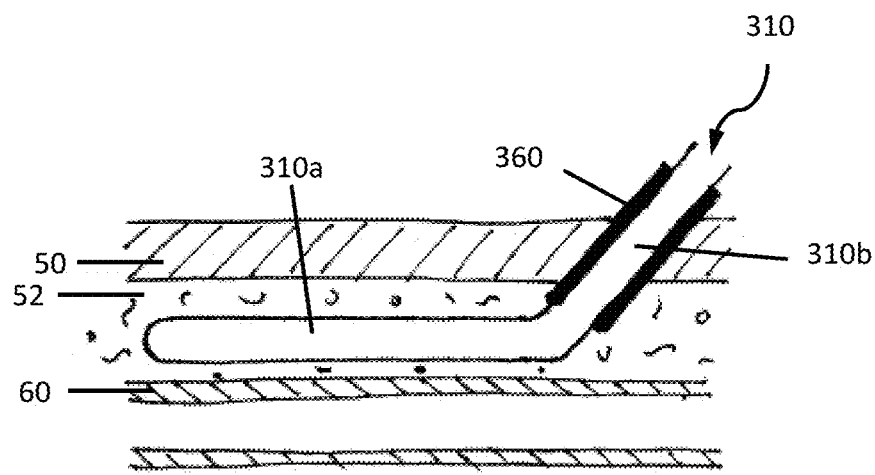
FIGS. 3A and 3B depict two variations of an internal cooling device.

A subcutaneous probe may include a treatment segment that may be inserted into adipose tissue in a variety of manners. For example, in some variations, as shown in FIG. 3A, the distal end of the probe may be located within adipose tissue. A treatment segment 310a of the probe 310 may be inserted through patient skin 50 into a selected portion of adipose tissue 52 overlying the target blood vessel 60. In some variations, the distal end of the probe may be located external to the patient. Probe 310 may include a proximal portion 310b overlaid with an insulator 360. Additionally or alternatively, the insulator may be provided on any desired portion of the probe 310 such as a portion of the treatment segment 310a of the probe.

The treatment segment 310a of the probe may be located at a distal end of the probe, and may be configured to allow the treatment segment of the probe to be inserted into the tissue such that it is generally parallel to the skin. In some variations, the treatment segment of the probe may be oriented at a non-zero angle relative to the rest of the probe body. For example, as shown in FIG. 3A, a proximal portion of the probe 310b may be oriented along a first axis, and the distal treatment segment 310a of the probe may be oriented along a second axis that is at a nonzero angle to the first axis. The proximal portion 310b may include an insulator 360 that helps maintain a temperature of a coolant prior to circulation through the distal treatment segment. The proximal portion 310b and the treatment segment 310a of the probe 310 may join at a vertex, a curved bend, or in any suitable manner. Alternatively, the treatment segment 310a of the probe 310 may be located at a distal end of the probe and aligned with the rest of the probe body 310b. In some variations, as shown in FIG. 3B, the treatment segment 310a of the probe may be any suitable segment of the probe, such as a straight medial portion of the probe.

Figure 3B:
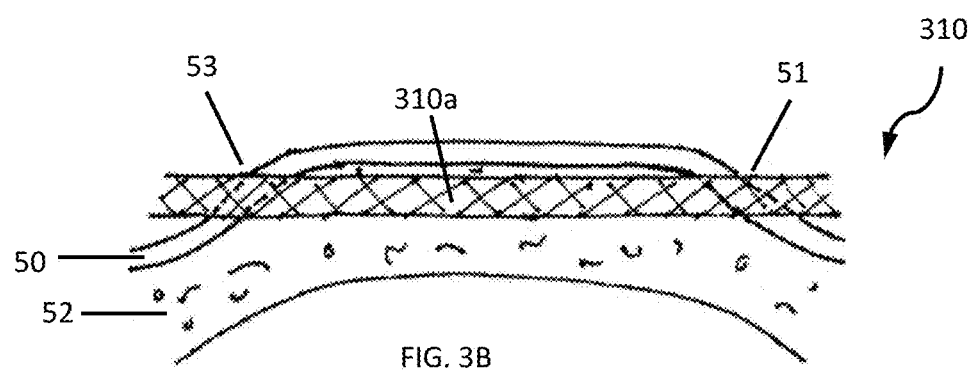

As shown in FIG. 3B, the probe 310a may be inserted through a first location 51 of patient skin 50 on one end of the adipose tissue 52 and continue to pass through tissue 52 to exit through a second location 53 of patient skin 50. In these and other variations, at least a portion of the external surface of probe 310 (i.e., the adipose tissue interface surface) may be in contact with and may cool the adipose tissue 52.

Figure 4:
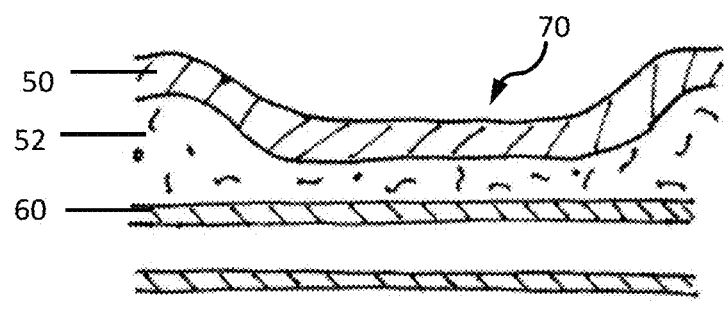
FIG. 4 is an illustrative depiction of a depression in adipose tissue overlying a target blood vessel.

As shown in FIG. 4, when this cooling process is maintained or repeated over a sufficient treatment period, as described in more detail herein, the selected portion of adipose tissue 52 overlying the target vessel 60 may be reduced, which may result in a depression 70 or "trench" in the adipose tissue 52 and skin 50. Beneath the depression 70, the target blood vessel 60 may be closer to the surface of the skin 50 than before treatment, thereby facilitating improved percutaneous access to the target blood vessel 60 in the region of the depression 70.

In some variations, the distal end of the treatment segment 310a may be blunt and atraumatic. This may reduce the risk of puncturing the target vessel with the probe 310. For example, the distal end of the treatment segment 310a may be blunt (e.g., may have semispherical or other rounded shape) in variations similar to that depicted in FIG. 3A in which the treatment segment 310a is at a distal end of the probe. However, in other variations the distal end of the treatment segment 310a may have a sharpened tip or other suitable tip.

The treatment segment 310a of the probe may be shaped similarly to the target blood vessel, particularly a treatment portion of the blood vessel 60 to which easier access is desired. In some variations, the treatment segment 310a of the probe 310 may be shaped such that when inserted into adipose tissue 52 between the skin 50 and the target vessel 60, the treatment segment 310a of the probe may be approximately aligned with and parallel to the treatment portion of the target vessel 60. For example, as shown in FIG. 3A, the treatment segment 310a of the probe 310 may be generally straight, in order to track a straight treatment portion of a target vessel. In other examples, the treatment segment of the probe may be curved in order to track a curved treatment portion of a target vessel, or may have any other suitable shape.

Generally, the probes described here may be configured to allow tissue 52 to be cooled for a sustained period of time. In order to do so, in some variations the probe may be configured to circulate a coolant. In these variations, the systems described here may comprise a temperature sensor and a cooling subsystem to achieve a desired temperature or temperatures, though they need not. In some variations, the probe may include a fluidic channel for carrying coolant. As shown in FIG. 1, for example, the fluidic channel may include a delivery lumen that carries the coolant toward a distal end of the treatment segment of the probe and a return lumen to carry the coolant away from the distal end of the treatment segment of the probe. In some variations, the delivery lumen and/or return lumen may extend at least substantially along the length of the treatment segment of the probe. In other variations, the delivery lumen and/or return lumen may additionally or alternatively extend along any other suitable portion of the probe or separate fluidic components. In some variations, the delivery lumen and/or return lumen may be approximately parallel and/or adjacent to one another along at least part of their lengths along the probe. However, the delivery and return lumens may carry coolant to and from the treatment segment of the probe in diverging directions, or in any suitable manner.

In some variations, the delivery lumen and the return lumen may be separate lumens that are in fluid communication with one another, such as at the distal end of the treatment segment. For example, as shown in FIGS. 5A and 5B, the delivery lumen 514 extends centrally along the body of the probe 510 and carries a fluid coolant 570 toward the treatment segment located at the distal end of the probe 510. The return lumen 516 is annular and concentric around delivery lumen 514, and receives coolant 570 from the treatment segment at the distal end of the probe 510 with coolant 570 flowing in the return lumen 516 in an opposite direction than in the delivery lumen 514. Alternatively, a delivery lumen 514 may be annular and concentric around a return lumen 516 that extends centrally along the body of the probe 510. The probe 510 may include additional structural features, such as one or more support fins 582, which may help maintain the shape of delivery lumen 514 and/or return lumen 516 for coolant flow.

In other examples, the probe may include any suitable arrangement of multiple lumens that may vary in shape, size, and number, such as those shown in FIGS. 6A-6G. The probe may include multiple delivery lumens 614 and multiple return lumens 616, as shown in an exemplary configuration in FIG. 6A. The ratio of the number of delivery lumens to the number of return lumens in the probe may be a ratio other than 1:1. For example, the probe may have two outer return lumens 616 and one central delivery lumen 614 as shown in FIG. 6B, or alternatively two outer delivery lumens and one central return lumen, or delivery and return lumens in any other suitable ratio. The delivery lumen 614 and return lumen 616 may have complementary cross-sections, such as approximately semi-circular with similar arc lengths (FIG. 6C) or unequal arc lengths (FIG. 6D).

Additionally, in some variations, the probe, delivery lumen, and/or return lumen may have a non-circular overall profile. For example, the overall profile of the probe may circumscribe a delivery lumen 614 and a return lumen 616 that are adjacent and laterally offset from one another, such as the probe of FIG. 6E that encloses two circular lumens or the probe of FIG. 6F that encloses two rectangular lumens. As another example, the probe may surround, but not closely circumscribe, a delivery lumen 614 and a return lumen 616 that are adjacent and laterally offset from one another, such as the probe of FIG. 6G that has an elliptical cross-section and defines circular delivery and return lumens. Although FIGS. 6A-6G distinctly identify each lumen as a delivery lumen 614 or a return lumen 616, it should be understood that each of the delivery and return lumens may be any particular lumen. Furthermore, other variations of the probe include other suitable combinations of features with respect to shape, size, and number of lumens.

Variations in which the probe has coaxial or otherwise adjacent delivery and return lumens may have a more uniform probe temperature. For example, as shown in FIGS.

5A and 5B, the probe 510 may maintain a substantially uniform probe temperature because the probe 510 thermally exposes the coldest coolant 570 entering the treatment segment of the probe in the delivery lumen 514 to the warmest coolant 570 exiting the treatment segment of the probe in the return lumen 516. In other variations, the probe may include insulation between the delivery and return lumens to reduce a warming effect of the warmer coolant in the return lumen on the cooler coolant in the delivery lumen.

Figure 7A:
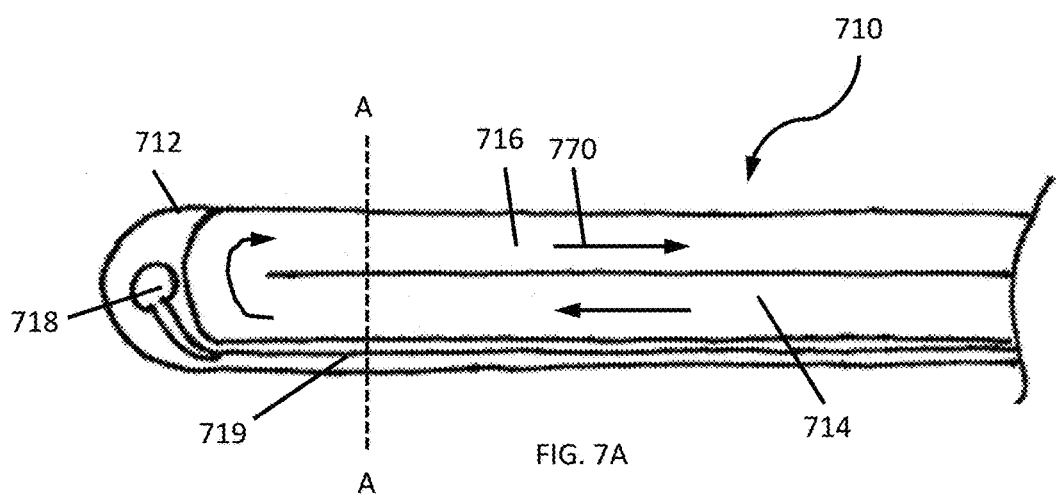
FIG. 7A depicts another variation of an internal cooling device with a temperature sensor.
Figure 7B:
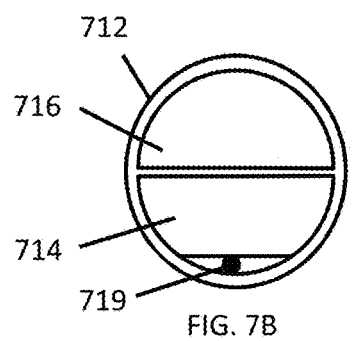
FIGS. 7B and 7C depict alternative cross-sectional views taken along line A-A of the internal cooling device depicted in FIG. 7A.
Figure 7C:
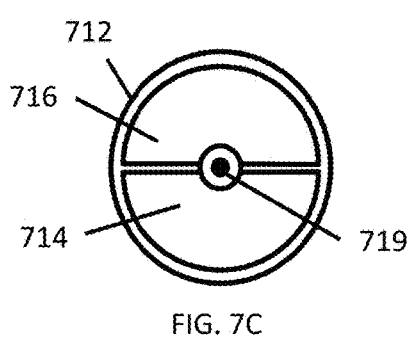

As shown in FIGS. 7A-7C, in some variations, the probe 710 may include a temperature sensor 718 to monitor temperature of the outer surface 712 of the probe 710 (i.e., the adipose tissue interface surface) and/or temperature of the coolant 770. The temperature sensor may be, for example, a thermocouple or a thermistor, and may communicate through sensor wire 719 to the control subsystem (not shown) which may modulate one or more parameters (e.g., flow rate, cooling rate in the cooling subsystem) of the system in order to achieve a particular temperature (e.g., to maintain a particular target temperature of probe and/or coolant, or to modulate the temperature of the probe and/or coolant). The sensor wire 719 may travel along the probe 710 to the sensor 718 in a lumen that is separate from the delivery lumen 714 and return lumen 716. For example, as shown in FIG. 7B, the sensor wire 719 may travel along a lateral lumen adjacent to the delivery lumen 714, or alternatively the lateral lumen may be adjacent to the return lumen 716. As another example, as shown in FIG. 7C, the sensor wire 719 may travel along a central lumen. However, in other variations, the sensor wire 719 may travel along the delivery lumen and/or return lumen, and may be protected from the coolant with insulation or in another suitable manner. In other variations, the temperature sensor may include any suitable kind of sensor and/or may communicate with the control subsystem wirelessly.

Although FIG. 7A depicts a single temperature sensor located on the distal end of the probe 710, in other variations of the probe, the temperature sensor may be located at any suitable point along the treatment segment or other suitable portion of the probe. Furthermore, in other variations, the probe 710 may include multiple temperature sensors. For example, the probe 710 may include multiple temperature sensors arranged at different respective axial and/or circumferential locations on the probe. At least some of the wires of multiple temperature sensors may travel independently along the probe (e.g., longitudinally at different circumferential locations) or may be bundled to travel together along the probe.

The probe may be structured to accommodate different kinds of coolant in the probe, including gaseous, liquid, and/or semi-solid or solid forms of coolant. In some variations, the probe may cool the surrounding adipose tissue by permitting the coolant to undergo phase changes as a result of absorbing heat from the tissue. For example, as shown in FIGS. 8A and 8B, the probe 810 may carry a liquid coolant 870L in an outer, annular delivery lumen 814 toward the treatment segment at the distal end of the probe that underlies skin 50.

Figure 8A:
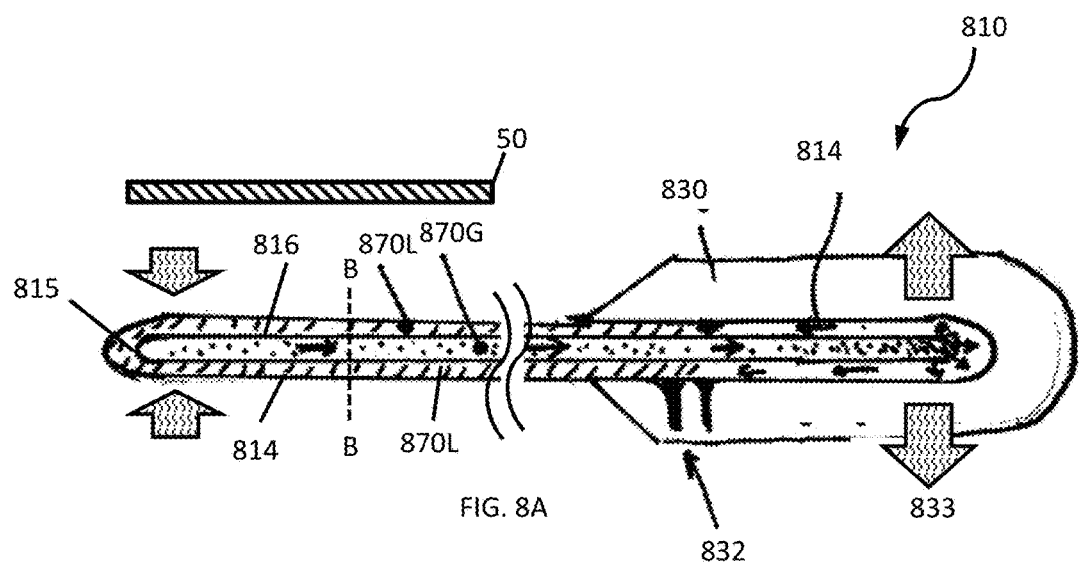
Figure 8B:
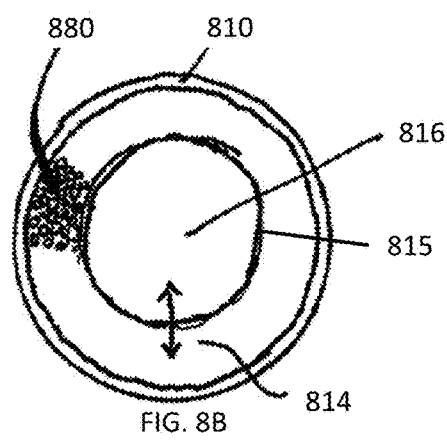

FIG. 8B is a cross-sectional view taken along line B-B of FIG. 8A. When passing through the treatment segment of the probe, coolant 870L absorbs heat from and cools the surrounding tissue, which may cause the coolant to vaporize. The wall 815 separating the delivery lumen 814 and the central return lumen 816 may be porous, such that the vaporized, gaseous coolant 870G passes through the porous wall 815 from the outer annular delivery lumen 814 into the central return lumen 816. Any suitable portion of the wall may be porous to allow transfer of coolant. The probe 810 then may carry the gaseous coolant 870G in the central return lumen 816 away from the treatment segment of the probe toward a proximal portion of the probe. In the proximal portion of the probe or a separate component in fluidic communication with the probe, a cooling subsystem (such as cold reservoir 830, as described further herein) may chill the coolant such that the coolant 870G releases heat 833 and condenses back into liquid coolant 870L. After cooling and condensing into a liquid phase, liquid coolant 870L may continue to circulate again through delivery lumen 814. This cycle of coolant vaporization and condensation may be repeated over time in order to reduce the temperature of the skin 50.

As another example, as shown in FIG. 8C, the probe 810 may use vaporization of pressurized coolant to induce a phase change in the treatment segment of the probe that absorbs heat from and consequently cools the surrounding tissue. As shown there, the probe 810 carries a liquid coolant 870L in a central delivery lumen 814 toward the treatment segment of the probe configured for insertion into adipose tissue underlying the skin. When passing through the treatment segment of the probe, coolant 870L absorbs heat from and cools the surrounding tissue, which may cause the coolant to vaporize. Similar to the example depicted in FIG. 8B, the wall 815 separating the delivery lumen 814 and the return lumen 816 may be porous such that the vaporized, gaseous coolant 870G passes through the porous wall 815 from the central delivery lumen 814 to the outer, annular return lumen 816.

Although FIG. 8C depicts only a distal portion of the wall 815 between the delivery and return lumens as being porous, all or any other suitable portion of the wall 815 may be porous to allow transfer of gaseous coolant 870G into the return lumen 816. The probe 810 may then carry the gaseous coolant 870G in the return lumen 816 away from the treatment segment of the probe. In some variations, the gaseous coolant 870G may be cooled and condensed by a cooling subsystem similar to that described above with reference to FIG. 8A. In another variation, as shown in FIG. 8C, the gaseous coolant 870G may be exhausted out of the probe 810. In this variation, the probe may comprise a valve 852 that modulates the exhaust of the gaseous coolant 870G. By controlling the rate of exhaust, the valve may control the pressure inside the probe and the rate at which the liquid coolant vaporizes, and therefore the valve may indirectly control the rate of heat transfer from the tissue to the coolant and the degree of cooling of the probe and surrounding tissue. The valve coupled to the return lumen 816 may control the rate of a phase transformation of the coolant 870G across the porous wall 815. Other aspects of flow control depicted in FIG. 8C including the liquid reservoir 870L and nozzle 854 are described in further detail later with respect to the coolant cooling subsystem.

In some variations of probes carrying liquid coolant, as shown in FIG. 8B, the liquid coolant 870L may be directed in the delivery lumen 814 through capillary action along a passive fluid distributor such as wick 880. The wick 880 may include, for example, porous sintered copper beads, but may additionally or alternatively include any suitable material for conducting liquid coolant 870L in the delivery lumen 814. In other variations, the probe 810 may include other mechanisms for inducing directional flow of liquid coolant 870L and/or gaseous coolant 870G, such as pressure differentials or temperature gradients. Furthermore, different variations of the probe 810, with different shapes, sizes, and/or relative orientations of the delivery lumen 814 and the return lumen

816 may similarly implement this principle of coolant vaporization and condensation to cool adipose tissue.

In other variations, the one or more delivery lumens and one or more return lumens may be integrated into a single lumen. For example, as shown in FIG. 6H, a single lumen probe may carry coolant both toward and away from the distal end of the treatment segment, by being coupled to multiple fluid distributors that collaborate to provide oscillating flow through the lumen. Such oscillating flow may similarly be implemented in lumens of multi-lumen probes. As another example, as shown in FIG. 9, a single lumen probe 910 may contain a solid or semi-solid coolant 970 in at least the treatment segment of the probe 910.

In some variations, as shown in FIG. 9, the probe 910 may carry a frozen coolant 970 (e.g., frozen gel or liquid) in at least the treatment segment of the probe 910. The frozen coolant 970 may have a melt or sublimation temperature such that the frozen coolant 970 undergoes phase change at a certain temperature (e.g., from solid to liquid or from solid to gas). This phase change may take advantage of latent heat of fusion in order to absorb energy and keep the probe 910 at a constant, cold temperature. In some variations, the frozen coolant 970 may be an insert that, when melted or sublimated, may be exchanged for another frozen coolant insert.

Figure 22A:
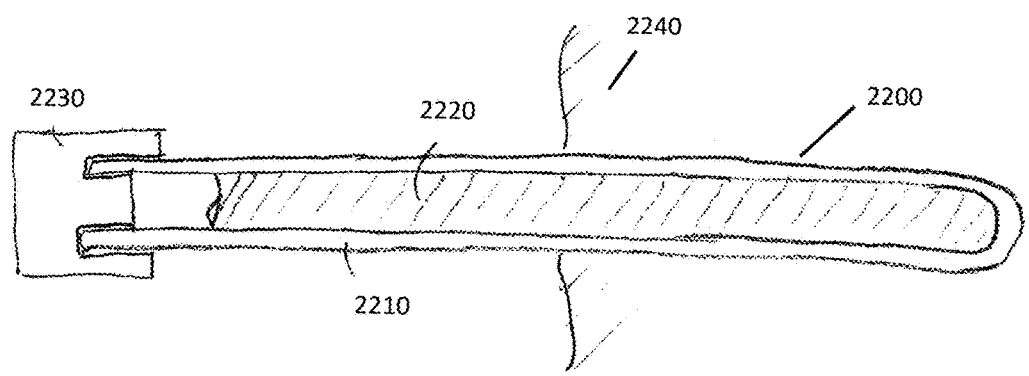
FIGS. 22A and 22B depict two variations of an internal cooling member.
Figure 22B:
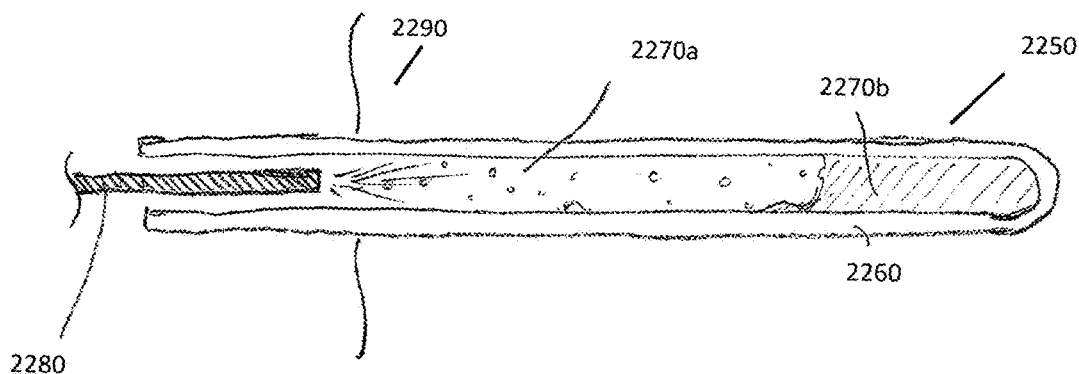

In some variations, as shown in FIGS. 22A and 22B, single lumen probes 2200, 2250 may be inserted into a patient body 2240, 2290 respectively. In FIG. 22A, a distal portion of the probe 2200 is inserted into the body 2240. A proximal portion of the probe 2200 is open-ended and may be closed by a detachable sealing member 2230 such as a cap. The coolant may be solid or semi-solid, and may be exchanged with new coolant or the probe may be replaced entirely with a new probe. In some variations, the probe is inserted between the surface of the skin and a target blood vessel such as a vein (not shown). In this manner, the probe may cool the adipose tissue between the skin and a blood vessel. In one example, the coolant may be ice or saline ice.

FIG. 22B shows an open-ended probe 2250, with an enclosed distal portion and an open-ended proximal portion. A distal portion of the probe 2250 is inserted into the patient body 2290. Coolant injector 2280 may inject a pressurized liquid coolant 2270a into a lumen of the probe 2250. As heat is absorbed from the body 2290 by the probe 2250, the liquid coolant 2270a will begin to undergo a phase change by boiling and condensing. The resulting vapor coolant 2270b will expand and will naturally be vented out of the open-ended proximal portion of the probe 2250, thereby reducing the temperature of the target adipose tissue.

The coolant injector 2280 may be removed from the probe 2250 after injecting coolant 2270a or may remain within the probe 2250, so long as the coolant vapor 2270b is able to vent out from the open-ended portion of the probe 2250. Additionally or alternatively, the coolant injector 2280 may continuously sputter liquid coolant 2270a into the tube or be inserted and removed from the probe 2250 periodically in a predetermined cycle to replace and replenish the coolant 2270a as needed. The coolant injector 2280 is not limited in shape so long as vapor coolant 2270b may vent from a proximal portion of the probe 2250. The probe 2250 may additionally or alternatively include a plurality of lumens such as those illustrated in FIGS. 6A-6G where liquid coolant 2270a is delivered through a delivery lumen and vapor coolant 2270b is vented out of the probe 2250 via a return lumen.

One more temperature sensors may also be provided to the probe 2200, 2250 to determine when the probe is no longer providing a desired cooling effect (e.g., when coolant has melted). A solid coolant 2220 may have a melt or sublimation temperature such that the coolant 2220 undergoes phase change at a certain temperature. The cooling members 2200 and 2250 may be formed of a biocompatible metal suitable for transferring heat such as those described elsewhere, including but not limited to stainless steel or a polymeric material, for example. Additionally, or alternatively, the cooling members illustrated in FIGS. 22A and 22B may be placed externally on a surface of the skin.

In some variations, the outer diameter of the treatment segment of the probe may be between approximately 3 millimeters and approximately 10 millimeters, or may be between 5 millimeters and 8 millimeters. In some variations, the length of the treatment segment of the probe may be at least approximately 10 millimeters to approximately 300 millimeters, or may be more than 300 millimeters. For example, the treatment segment of the probe may be approximately 6-7 millimeters in diameter and 100 millimeters long. However, the overall dimensions of the probe may vary based on the characteristics of the area in which the probe will be inserted, as well as various aspects of the probe and coolant. For example, some factors affecting the desired size of the probe include the thickness of the adipose tissue (correlating to depth of the target blood vessel under the skin), length and diameter of the treatment portion of the target blood vessel, and thermal characteristics of the material of the probe (e.g., thermal conductivity, wall thickness) and coolant (e.g., specific heat capacity, flow rate). Accordingly, the above-listed dimensions are only exemplary, and may vary depending on the specific application of the device and system.

In some variations, at least the adipose tissue interface surface of the probe may include a biocompatible metal suitable for transferring heat from surrounding tissue to the coolant within the probe, and therefore effectively cooling the surrounding tissue. For example, the probe may include stainless steel (e.g., grade 316L), stainless steel clad copper, or stainless steel clad aluminum. In other variations, the probe may include a polymeric material. Generally speaking, the probe may be a rigid or a semi-rigid material, but in other variations, the probe may be flexible. However, the probe may generally include any suitable combination of materials. In some variations in which the probe is flexible, the probe may additionally include a stylet and/or a guidewire to help navigate the probe to the treatment area.

Although the system is generally shown in the figures as having one probe, in other variations, the system may include two or more probes. In some variations, multiple probes may be placed in series in the tissue overlying the target blood vessel, such as to track the curvature of blood vessel. Additionally or alternatively, each probe may be placed in the tissue overlying a respective target blood vessel, such as to perform cryolipolysis above multiple blood vessels simultaneously.

Guide Member

In one variation, the system may include a guide member to help position treatment segments of the fluidic channel appropriately over the target blood vessel. In some variations, as shown in FIGS. 15A and 15B, the system may comprise a guide member 1568 configured to help guide the positioning and/or orientation of the probe 1510 of the device 1502 in the adipose tissue of the patient. For instance, the guide member 1568 may be used to position the probe at a particular depth in the adipose tissue 52 to target a selected portion of tissue, to help prevent the probe 1510 from damaging the target vessel 60 and other tissue whose protection is desired, and/or any suitable purpose. The guide member may additionally or alternatively be used to help position the probe at a particular rotational orientation (e.g., to position the insulator 1564). In some variations, the guide member 1568 may include a magnetic material, such as a permanent magnet or a ferromagnet that repels and/or attracts one or more components of the cooling device 1502. The guide member 1568 may, for example, include a magnetic material that repels or attracts at least a portion of the probe 1510 (or a component coupled to the probe, such as insulator 1564).

As another example, the guide member 1568 may repel a first portion of the probe 1510 or component coupled to the probe 1510, and the guide member 1568 may further attract a second portion of the probe 1510 or component coupled to the probe. However, the guide member 1568 may interact with the probe 1510 in any suitable manner. The size and shape of the guide member 1568 may vary depending on the specific application. For example, a magnetic guide member 1568 may induce a stronger repelling or attracting magnetic force against the probe 1510 (e.g., by having a larger size or greater magnetic strength), in applications in which the controlling magnetic force traverses a greater amount of tissue between the guide member 1568 and the probe 1510 when inserted into the patient. That is, when the layer of adipose tissue between the probe and the exterior surface of the skin is greater.

For a guide member 1568 comprising one or more permanent magnets on the skin surface 50, ultrasound may be used to identify and mark the location of the target vessel on the skin surface 50. The permanent magnets of guide member 1568 may be attached to the skin surface over the target vessel by way of straps and/or adhesive, for example. The guide member 1568 may all be magnetic or have one or more portions that are magnetic. In one variation, an incision may then be made in the patient for insertion of a cooling probe under the skin 50 and tunneled. The probe 1510, having a the tip which may be flexible, may be guided by the permanent magnets of the guide member 1568 under the skin surface 50 through an attractive force between the two such that the cooling probe tunnels and resides in a desired location above the target vein segment during a treatment session. As a secondary effect, the attractive magnetic force between the guide member 1568 magnet and the probe 1510 may in some instances compress the interposed tissue to reduce blood flow between the two structures, thereby facilitating greater cooling of the interposed tissue.

As shown in FIG. 15A, in one variation, the guide member 1568 may be external to the patient, such that the guide member 1568 may be moved along the surface of the skin 50 (or another external surface) and guide the position and/or orientation of the probe 1510 through the skin 50 and any tissue located between the probe 1510 and the skin 50. As shown in FIG. 15B, in another variation, the guide member 1568 may be inserted into the treatment portion of the target vessel 60 itself, under the probe 1510 and used to locate the probe 1510 adjacent to the vessel 60. In this variation, the guide member 1568 may repel at least a portion of the probe 1510, such as to help prevent the probe 1510 from approaching too close and risk damaging the target vessel 60. In yet another variation, the guide member 1568 may be inserted in another portion of the adipose tissue or other internal patient tissue in order to interact with and guide the probe 1510.

Alternatively, the guide member 1568 may repel the probe through magnetism from touching the vessel surface if it were desirable to prevent direct cooling of the vessel tissue.

In yet another variation, the guide member 1568 in the vessel 60 may be used to rotationally orient the probe 1510 relative to the vessel such that an insulative portion of the probe 1510 is positioned to reside between the active cooling probe 1510 and the vessel 60 wall. Again, rotational alignment forces may be induced via magnetism.

In some variations, the system may comprise a reference marker to help position the probe using imaging techniques. In some variations, as shown in FIG. 15C, the reference marker 1569 may be coupled to the probe, or may be coupled to a component coupled to the probe. For example, the imaging marker 1569 may be a cylindrical radiopaque marker coupled circumferentially around the treatment segment of the probe 1510. The radiopaque marker 1569 may be visible under fluoroscopy or other imaging modalities. The radiopaque marker may include, for example, tantalum, and/or suitable radiopaque materials. Although the imaging marker depicted in FIG. 15C is ring-shaped, the imaging marker may be rectangular or any other suitable shape. Furthermore, in other variations, the imaging marker may be an etching (e.g., a cross-mark) on the probe 1510 or other component coupled to the probe 1510.

External Cooling Devices

Figure 17:
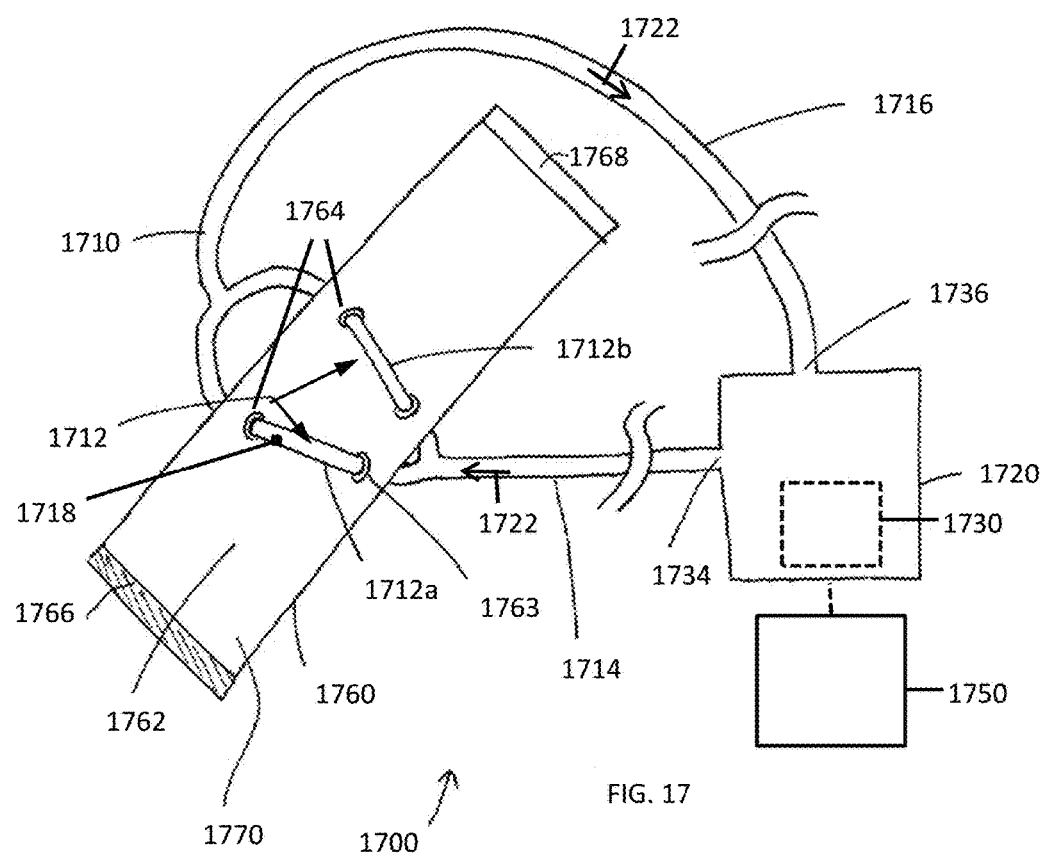
FIG. 17 depicts one variation of a system for facilitating percutaneous access to blood vessels with an external cooling device.

Also described herein are external cooling devices and systems. As shown in FIG. 17, in some variations, an external cooling device for facilitating percutaneous access to a target blood vessel in a patient may comprise a cooling member 1710 with an elongate fluidic channel 1712 to carry a coolant, and a securing member 1760 to couple the cooling member 1710 to an external surface of the patient (not shown). In some variations, as described further below, the coolant may be a fluid such as a liquid or gas, but in other variations, the coolant may be a solid or a semi-solid, such as a gel. The fluidic channel may include one or more treatment segments (e.g., 1712a or 1712b) to cool a selected portion of adipose tissue, and the securing member 1760 may be configured to couple at least a portion of the cooling member 1710 to the patient such that the treatment segment of the fluidic channel overlies and is substantially aligned with a treatment portion of the target blood vessel. In such a configuration, the treatment segment of the fluidic channel may provide an external cooling source to cool and, over time, reduce the volume of tissue overlying the treatment portion of the target blood vessel. In some variations, the external cooling device may be part of a system 1700 that further includes a cooling subsystem 1720 with a cooling mechanism 1730 that modifies the temperature of the coolant and a pump that receives coolant from the cooling mechanism and delivers coolant to the probe. In some variations, the system may further include a control subsystem 1750 that controls the flow rate and/or temperature of the coolant.

Cooling Member

As shown in FIG. 17, the cooling member 1710 may include a fluidic channel 1712 such as tubing configured to carry a coolant 1722. The cooling member 1710 may include one, two, three, or more than three treatment segments, where each treatment segment is configured to provide an external cooling source to cool adipose tissue overlying a respective treatment portion of a target blood vessel. Some treatment segments may be configured to provide supplementary cooling sources to cool adipose tissue overlying the same portion of a target vessel. In some variations, such as that as shown in FIG. 17, the cooling member 1710 may be configured to target adipose tissue overlying the basilic vein and the cephalic vein in the upper arm of the patient. In this variation, the fluidic channel 1712 may include a first treatment segment 1712*a* and a second treatment segment 1712*b*. The first treatment segment 1712*a* may be configured to track a treatment portion of the cephalic vein, and the second treatment segment 1712*b* may be configured to track a treatment portion of the basilic vein. Accordingly, the relative orientations of the first and second treatment segments of the fluidic channel may be similar to that of the cephalic and basilic veins. However, in other variations, the size, shape, and number of treatment segments of the fluidic channel 1712 may vary depending on the application. For example, the first and second treatment segments 1712*a* and 1712*b* may be parallel. As another example, the fluidic channel 1712 may include only one treatment segment.

In some variations, the cooling member 1710 may include a temperature sensor 1718 (e.g., thermocouple or thermistor) that measures the temperature of the coolant 1722 and/or cooling member 1710 at any point along the cooling member 1710. For example, as shown in FIG. 17, the temperature sensor may be located on an internal or external surface of a treatment segment (e.g., 1712*a* or 1712*b*) or on an internal or external surface of another portion of the fluidic channel 1712. In some variations, the cooling member 1710 may include multiple temperature sensors arranged at multiple locations along the cooling member 1710. Similar to the system including an internal cooling device described above, the measured one or more temperatures of the coolant 1722 and/or cooling member 1710 may be provided to the control subsystem 1750.

The fluidic channel 1712 may have any suitable diameter. For example, the fluidic channel 1712 may have an inner diameter between about ⅛ inch and about ½ inch, or between about ¼ inch and about ⅜ inch. In some variations, the fluidic channel 1712 may comprise a flexible material, such as polypropylene, nylon and/or other suitable flexible materials (e.g., PVC, Tygon, silicone, deformable copper or stainless steel tubing, or the like). When the fluidic channel 1712 comprises a flexible material, it may be configured to conform to the patient's tissue, and/or may be configured to be shaped to trace the target vessels (e.g., the basilic and/or cephalic veins). However, it should be appreciated that in some variations, the tubing may be made from a rigid or semi-rigid material.

In yet other variations, the internal configuration of the probes disclosed in FIGS. 5-9 and 22 such as the size, shape and number of lumens may be provided as the internal configuration of the external cooling member as well.

Securing Member

A securing member may be configured to directly or indirectly couple a cooling member to an external surface of the patient such that a treatment segment of the fluidic channel overlies and is substantially aligned with a treatment portion of the target blood vessel. In other words, the securing member may secure the treatment segment of the cooling member against the skin overlying the treatment portion of the target vessel. In other variations, the securing member may be omitted. For example, the cooling member may independently couple to the patient, such as by self-adhering to the skin of the patient.

As shown in FIGS. 17 and 18, in some variations, the securing member may comprise a cuff that is configured to couple to the patient with a radially compressive force. For example, as shown in FIG. 17, cuff 1770 may couple to the cooling member 1710 and wrap around a limb (e.g., upper arm) of the patient. The cuff 1770 may include a tissue interface side 1762 that is configured to contact an external surface (e.g., skin) of the patient, and a second side opposite the tissue interface side 1762. In this variation, the cuff 1770 may wrap around a limb of the patient and secure the cooling member 1710 in place by joining the first end 1766 with the second end 1768 of the cuff 1770. The first and second ends 1766 and 1768 may couple to one another with hook and loop fastener, ties, hooks and eyes, belt loops, zippers, snaps, and/or any suitable fasteners. Additionally or alternatively, the cuff 1770 may include a tubular sleeve that slips over the limb of the patient and secures to the patient with elastic, cinching ties, and/or any suitable fastener. As shown in FIGS. 18A-18C, the first end 1866 and the second end 1868 of the cuff 1870 may join in a manner similar to the joining mechanisms of the first end 1766 and second end 1768 of cuff 1770 depicted in FIG. 17.

Figure 19:
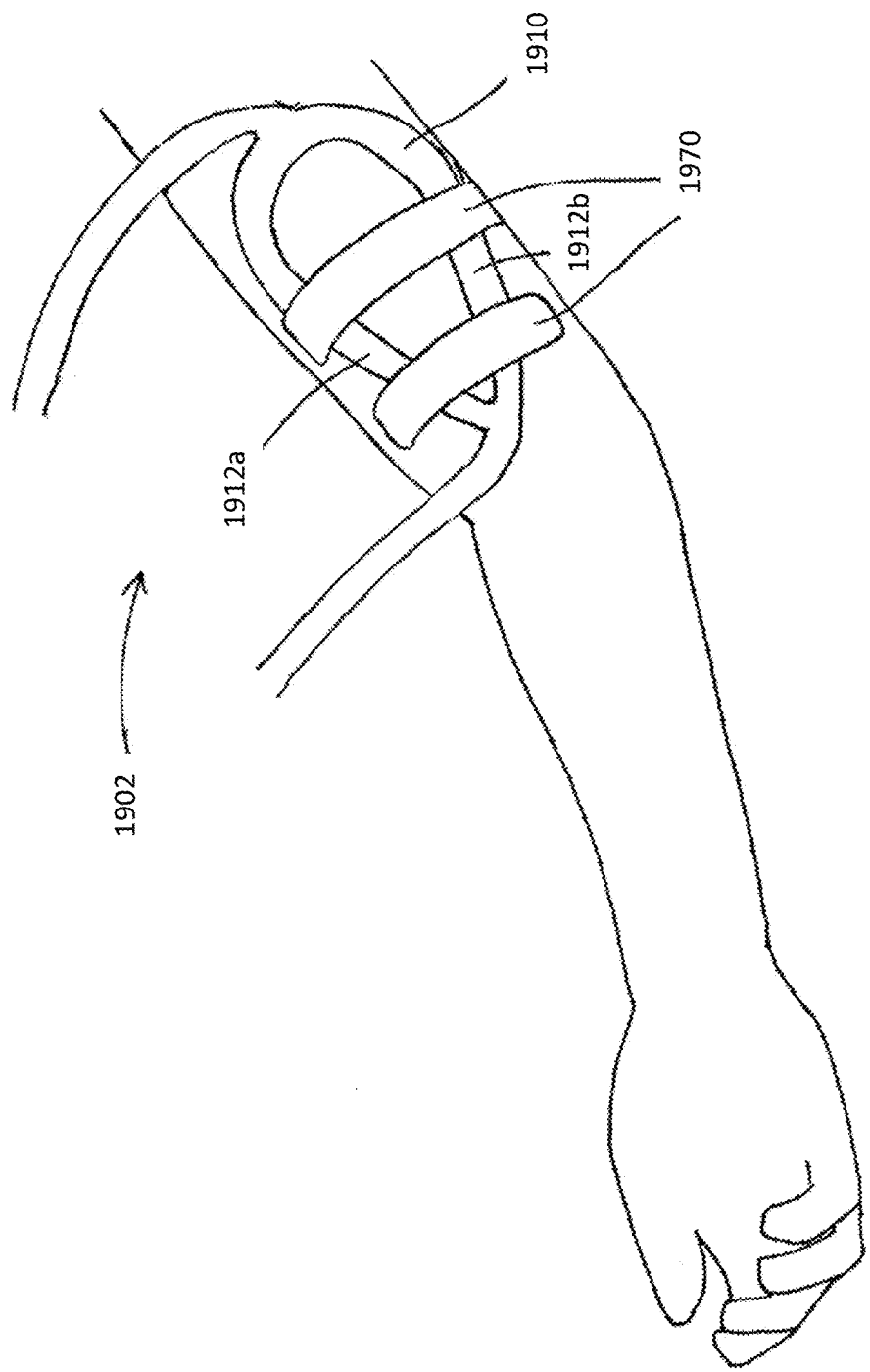
FIG. 19 depicts another variation of an external cooling device and another variation of a securing member.

As shown in FIG. 19, in some variations, the securing member 1902 may include at least one adhesive dressing which may be applied to the cooling member 1910. For example, in the variation depicted in FIG. 19, the securing member may include one or more adhesive strips 1970 that are configured to adhere to an external surface of the patient and hold the one or more treatment segments 1912 against the patient. The strips may be applied cross-wise relative to the treatment segments or longitudinally along the treatment segments, or in any suitable orientation. In some variations, the one or more adhesive dressings may be large and cover all or a substantial portion of the entire treatment segment 1912 and/or other portions of the cooling member 1910. In some variations, the one or more adhesive dressings may be pre-attached to the cooling member 1910 such that the relative positions of any multiple treatment segments 1912 may be established prior to their placement on the patient. In other variations, the one or more adhesive dressings may be attached to the cooling member 1910 after placing the one or more treatment segments 1912 on the patient, such that the relative positions of any multiple treatment segments 1912 may be adjusted before being secured to the patient by the adhesive dressings 1970.

Figure 18A:
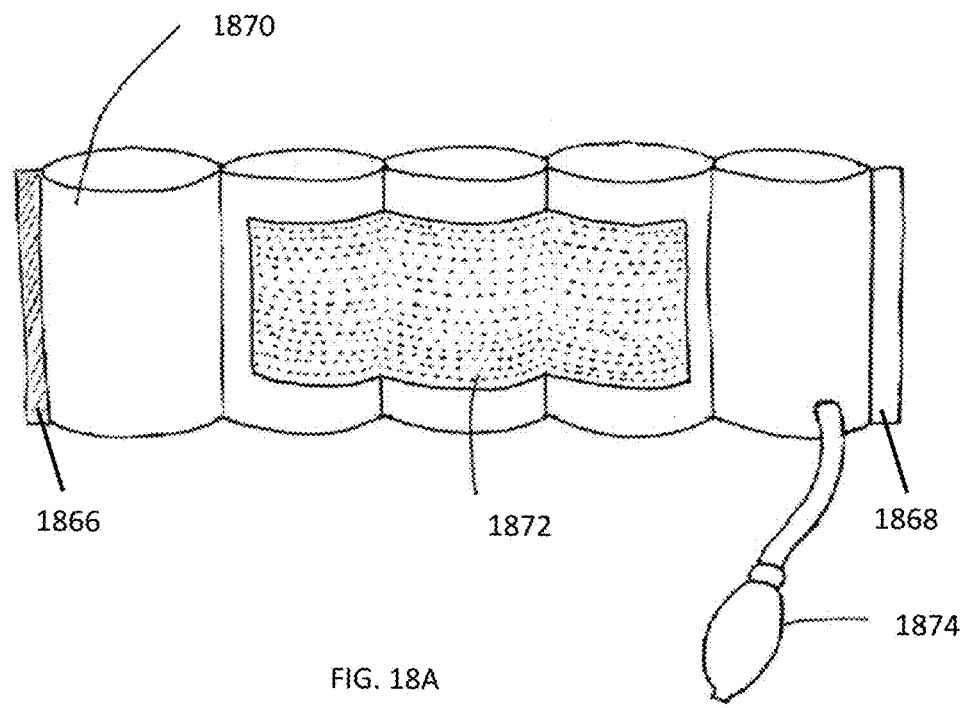
FIGS. 18A-18C depict variations of a securing member.

In some variations, the securing member may be circumferentially adjustable, to accommodate patient limbs of a variety of sizes and/or to enable variable compressive force of the cooling member against the skin. Increasing the compressive force of the treatment segments of the fluidic channel may force the treatment segments deeper into the tissue of the patient, thereby increasing the depth at which tissue cooling occurs. In one variation, as shown in FIG. 18A, the securing member may include an inflatable cuff 1870 that wraps around a limb (e.g., upper arm) of the patient. The inflatable cuff may include one or more inflatable cells adjustable in volume ranging from a deflated configuration, a partially inflated configuration, and a fully inflated configuration. Inflation may be controlled, for example, by one or more hand pumps 1874, but may additionally or alternatively be controlled by an automated pump. In versions of cuffs with multiple cells, each cell may have its own respective inflation pump. The cells may be shaped with a flexible inner wall such that generally speaking, a higher degree of inflation in the cuff will result in a smaller internal circumference of the cuff that presses the cooling member more forcefully against the tissue of the patient. The one or more cells may be fluidically connected such that all cells are inflated in tandem.

Alternatively, each of the cells may be independent structure such that some of the cells may be at least partially inflated while other cells may be completely deflated. Such separate, independent adjustability may enable different degrees of compression (and different depth ranges of cooling) for different portions of the fluidic channel. For example, one cell may be coupled to or overlie a first treatment segment of the fluidic channel that corresponds to a first target vessel, while a second cell may be coupled to or overlie a second treatment segment of the fluidic channel that corresponds to a second target vessel. In this example, if the two cells are inflated to different degrees, the resulting differential compressive forces on the first and second treatment segments against the skin of the patient may enable different depths of cooling. Such selective different depths of cooling may be desirable, for example, if the two target vessels are located at different tissue depths. In various versions, the inflatable cuff may include a multi-dimensional array of inflatable cells (e.g., a rectangular grid) acting like "pixels" of inflation pattern resolution to permit a range of selective circumferential adjustability over the surface area of the cuff.

Figure 18B:
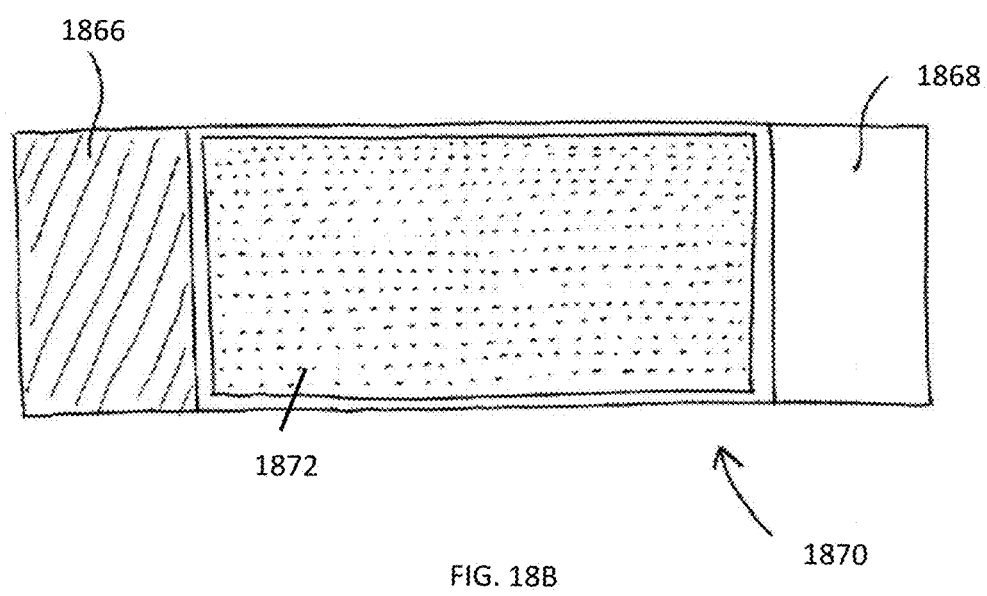

In another variation of an adjustable securing member, as shown in FIG. 18B, an adjustable cuff 1870 may secure the cooling member in place by joining the first end 1866 with the second end 1868, overlapping the first and second ends to varying degrees. For instance, in some positions, the first and second ends may fully overlap, which results in a decreased circumference of cuff 1870 and increased compressive force. In other positions, the first and second ends may only partially overlap, resulting in an increased circumference of cuff 1870 and decreased compressive force. The first and second ends 1866 and 1868 may couple to one another with hook and loop fastener, ties, hooks and eyes, belt loops, zippers, snaps, and/or any suitable fasteners.

In some variations, the securing member may fix the position of one or more segments of the fluidic channel. In one variation, as shown in FIG. 17, at least a portion of the fluidic channel may be threaded through the securing member. For example, in the variation depicted in FIG. 17, the first treatment segment 1712a and the second treatment segment 1712b of the fluidic channel may each thread through a respective series of openings 1764 on the securing member 1760 between a tissue interface surface 1762 of the securing member and the surface opposite the tissue interface surface (not shown). This arrangement may fix the relative positions of the one or more treatment segments 1712a and 1712b on the securing member 1770. Furthermore, this arrangement may isolate the one or more treatment segments 1712a and 1712b on the tissue interface surface 1762, which may enable the one or more treatment segments to directly contact and focus their cooling effect to only the skin of the patient overlying a target vessel. However, in some variations, the securing member 1770 may permit some repositionability of the fluidic channel 1712 by providing an array of openings 1763 through which the fluidic channel segments may be selectively threaded, such that one or more of the fluidic channel segments is repositionable.

Figure 18C:
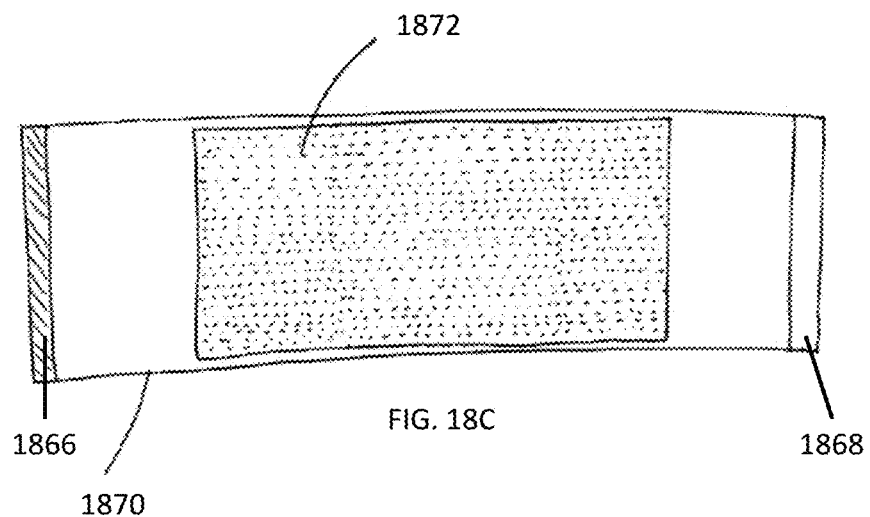
Figure 18D:
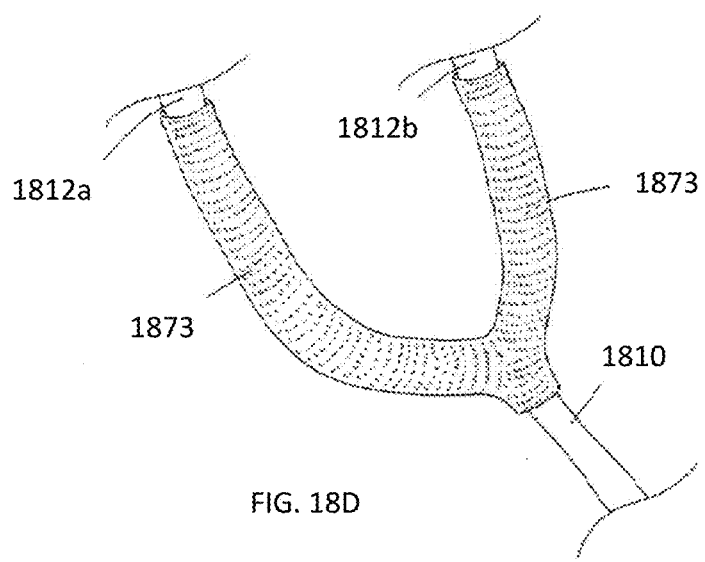
FIG. 18D depicts a variation of an external cooling device to be used with one of more variations of a securing member.

In other variations, the securing member may enable repositioning of one or more segments of the fluidic channel on the securing member. For example, as shown in FIGS. 18A-18C, the securing member may include an attachment region 1872 to which the treatment segments 1812a and 1812b shown in FIG. 18D may be removably connected in various orientations. Although the securing member 1870 of FIGS. 18A-18C includes a single rectangular attachment region 1872, it should be appreciated that the securing member 1870 may include any suitable number of attachment regions in any suitable pattern and shapes.

In some variations, the attachment region 1872 may be larger than the treatment segments 1812, such that the treatment segments 1812 may be positioned in more than one location on the attachment region 1872, and/or in more than one relative orientation. For example, the first treatment segment 1812a and the second treatment segment 1812b in FIG. 18D from respective branches 1873 may be positioned closer or farther away from one another, and/or at greater or smaller angles relative to one another, on an attachment region. Branches 1873 may meet at fluidic channel 1810. The distance and/or orientation of the treatment segments on the attachment region may depend on the specific application (e.g., the anatomy of the patient). In variations in which the securing member enables repositioning of one or more segments of the fluidic channel on the securing member, the fluidic channel segments may couple to the securing member with hook and loop fastener (e.g., hook or loop may be wrapped fully or partially circumferentially around the fluidic channel segments), adhesive tape, low-strength epoxy, and/or any suitable reversible manner.

In some variations, the securing member may include a temperature sensor, such as to measure the temperature of the skin on or near the treatment region overlying the target blood vessel. The temperature sensor may include a thermocouple, a thermistor, or any suitable sensor. In one example, a temperature sensor may be located on a tissue interface surface (e.g., surface 1762 as shown in FIG. 17) such that when the securing member is coupled to the patient, the temperature sensor is adjacent to the skin of the patient. In some variations, the securing member 1770 may include multiple temperature sensors arranged at multiple locations on the securing member. For example, a temperature sensor may be provided additionally or alternatively in the securing member at a location to measure the temperature of the cooling member. Similar to the system including an internal cooling device described above, the measured one or more temperatures may be provided to the control subsystem.

Coolant and Cooling Subsystem

As described above, coolants of various kinds may be used to cool the internal probe and/or the external cooling member and the surrounding tissue. A discussion of variations of the coolant and cooling subsystem for an internal probe is presented first and followed by variations of the coolant and cooling subsystem for an external cooling member.

In variations in which coolant is circulated through the probe, the cooling subsystem may include a cooling mechanism and a fluid distributor. The cooling mechanism may modify the temperature of the coolant, and the fluid distributor may deliver the coolant from the cooling mechanism to the probe. The cooling subsystem may be located in a separate unit in fluidic communication with the probe with tubing or other fluidic channels (e.g., cooling subsystem 220 depicted in FIG. 2 in communication with probe 210), and/or integrated with a proximal portion of the probe (e.g., as shown in FIGS. 8A-8C). Furthermore, various features of the cooling subsystem, such as cooling fins or other heat sinks, may additionally or alternatively be arranged anywhere along the fluidic pathway of the coolant to chill the coolant.

Figure 10A:
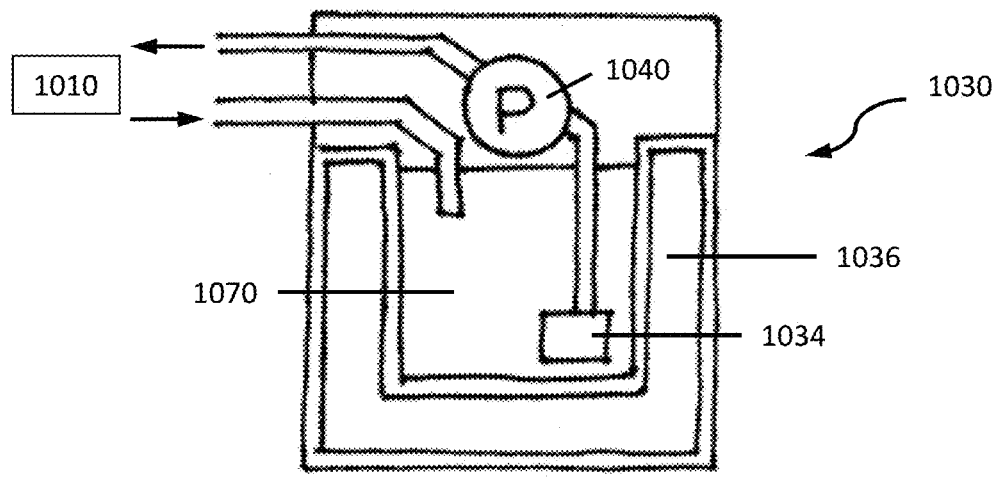
FIGS. 10A and 10B depict variations of a cooling subsystem.
Figure 10B:
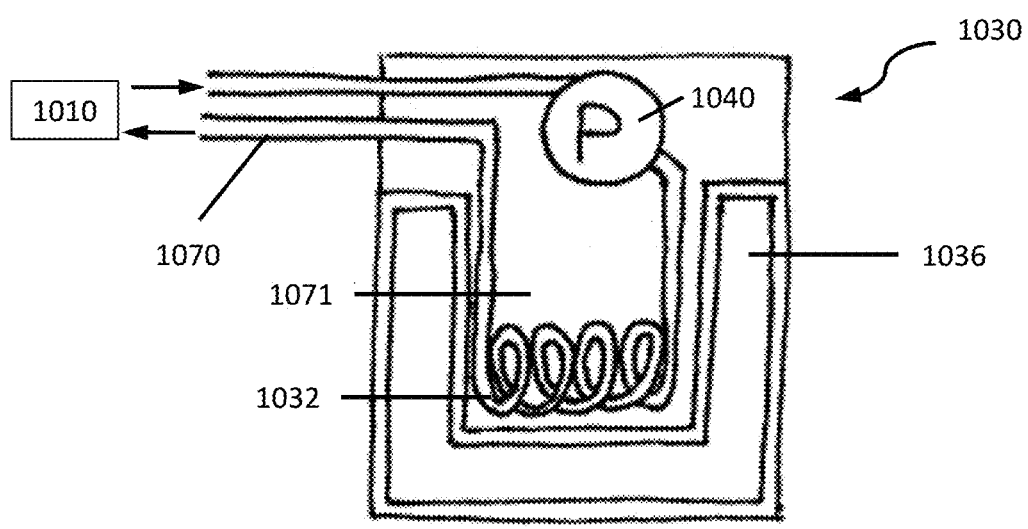

In some variations, as shown in FIGS. 10A and 10B, the cooling mechanism 1030 may include a cooling tank 1036 and the fluid distributor 1040 may include a pump. In a first example shown in FIG. 10A, in an open fluidic system, the cooling tank 1036 may include a reservoir of coolant (e.g., a liquid coolant) that is in fluid communication with the probe 1010. In this example, the cooling tank 1036 may include a filter 1034 to purify and/or reduce particulates and other matter from the coolant 1070 before the coolant 1070 is pumped into the probe 1010. The cooling tank 1036 may include a heat pump, ice, and/or other suitable setup for cooling the coolant 1070 or other fluid in the reservoir 1036. The reservoir may be insulated with expanded polystyrene foam, a double-walled structure, and/or other suitable insulation materials. As depicted in FIG. 10A, the pump 1040 may be configured to actuate the coolant 1070 from the cooling tank 1036 from a downstream location relative to the cooling tank 1036. The fluid distributor 1040 may be, for example, a centrifugal pump, a positive displacement pump, a peristaltic pump, or any other suitable pump. In this example, the fluid distributor 1040 may actuate coolant 1070 from the cooling tank 1036 and deliver the coolant 1070 to the probe 1010. After circulating in the probe 1010, the coolant may return from the probe 1010 and flow into the cooling tank 1036, which chills the coolant 1070 to be recirculated in the probe 1010 by fluid distributor 1040.

In a second example, as shown in FIG. 10B, in a closed fluidic system, the cooling tank 1036 may include a heat exchanger 1032 that transfers to the surrounding medium 1071 (e.g., a second coolant) the heat from the coolant 1070 circulating within the heat exchanger 1032, thereby cooling the coolant 1070. The cooling tank 1036 may be similar to the tank described above in reference to FIG. 10A, or any suitable variation. As depicted in FIG. 10B, the fluid distributor 1040 may be configured to actuate the coolant 1070 through the cooling tank 1036 from an upstream location relative to the cooling mechanism 1036. In this example, the fluid distributor 1040 may actuate coolant 1070 from the probe 1010 to pass through the heat exchanger 1032 and deliver the chilled coolant 1070 to the delivery lumen of the probe 1010. After circulating in the probe 1010, the coolant 1070 may flow from the probe 1010 into the fluid distributor 1040, which then actuates the coolant 1070 toward the heat exchanger 1032 to be chilled and to recirculate in the probe 1010.

In other variations, the cooling subsystem 1030 may be integrated into a proximal portion of the probe. For example, as shown in FIG. 8A, a portion of the probe 810 that is proximal to the distal treatment segment of the probe may be coupled to one or more heat sinks. In particular, the proximal portion of the probe 810 may include a cold reservoir 830 (e.g., a scaled-down version of the cooling tank of FIG. 10B) and/or cooling fins 832. The cold reservoir, cooling fins, and/or other heat sinks may absorb heat from the coolant flowing in or from return lumen 816, thereby chilling the coolant 870 prior to recirculation in the probe 810.

In yet other variations, the coolant may originate from a reservoir that can be exchanged as the coolant needs replacement due to exhaustion or eventual warming of the reservoir. For example, as shown in FIG. 8C, a reservoir of chilled coolant 870L may be attached directly to the delivery lumen 814 of the probe 810. The variation depicted in FIG. 8C includes a fluid-tight, threaded connection 853 between the reservoir of chilled coolant 870L and a proximal portion of the probe 810, and a nozzle 854 that may help control flow of the coolant 870L into the probe, but other variations may additionally or alternatively include any suitable kind of connection, such as one with gaskets and/or valves.

In other variations, coolant may not circulate through the probe. In some of these variations, the probe may be replaced during the procedure in order to maintain the desired temperature. For example, as described above with respect to FIG. 9, in variations in which a probe 910 carries a frozen coolant insert 970, the frozen coolant insert 970 may be exchanged for another probe when the coolant insert 970 melts. Similarly, in the variation shown in FIG. 22A, the probe 2200 may be replaced with a new probe.

Next, for variations of a cooling device comprising an external cooling member, coolants of various kinds may be used in the treatment segment of the cooling member to cool tissue. As shown in FIG. 17, in some variations, the coolant 1722 may include a fluid that circulates throughout the cooling member 1710 and is chilled by cooling subsystem 1720. The fluidic channel 1710 may include a delivery channel 1714 and return channel 1716. Delivery channel 1714 delivers chilled coolant 1722 from outlet 1734 of cooling subsystem 1720 to the one or more treatment segments (e.g., 1712a and 1712b). Return channel 1716 receives the coolant 1722 from the one or more treatment segments and returns the coolant to the inlet port 1736 of cooling subsystem 1720. Cooling subsystem 1720 may chills the coolant 1722 in preparation for recirculation into the treatment segments.

Although FIG. 17 depicts a single delivery channel 1714 that diverges into multiple treatment segments and a single return channel 1716 that is formed by the merging of multiple treatment segments, in other variations each treatment segment may be in fluidic communication with a respective delivery channel 1714 and/or respective return channel 1716. Accordingly, cooling subsystem 1720 may include multiple outlet ports 1734 and/or multiple inlet ports 1736. In some variations, the delivery channel 1714 and/or the return channel 1716 may be integrally formed with the treatment segments 1712, while in other variations the delivery and/or return channels are separate components that are fluidically coupled to the treatment segments.

In some variations, the cooling subsystem 1720 may include cooling mechanism 1730, similar to that described above with respect to systems including an internal cooling device (e.g., the cooling subsystems described with reference to FIGS. 8-10). For example, the cooling mechanism 1730 may be similar to cooling mechanism 1030 shown in FIG. 10A having an open fluidic system, in which the cooling tank 1036 includes a reservoir of coolant (e.g., a liquid coolant) that is in fluid communication with the cooling member 1010.

As another example, the cooling mechanism 1730 may be similar to cooling mechanism 1030 shown in FIG. 10B having a closed fluidic system, in which the cooling tank 1036 includes a heat exchanger 1032 that transfers to the surrounding medium 1071 (e.g., a second coolant fluid) the heat from the coolant 1070 circulating within the heat exchanger 1032, thereby cooling the coolant 1070. However, any other suitable cooling subsystems may additionally or alternatively be included in the system.

For both a subcutaneous probe and cooling member, the coolant may be a liquid, vapor, or semi-solid or solid. Furthermore, as shown in FIGS. 8, 9, and 22A-22B, the coolant may undergo a phase change while cooling the probe and surrounding tissue, such that the coolant may take different forms at different locations in the probe, cooling member and cooling subsystem. Some exemplary coolant substances include saline, polyethylene glycol, and isopropyl alcohol. However, any suitable refrigerant or other coolant may be used.

Generally, the coolant used in the subcutaneous probe and the cooling member may have a temperature between about $-10°$ F. and about 50° F. In some variations, the coolant may have a temperature between about 0° F. and about 40° F. In other variations, the coolant may have a temperature between about 10° F. and about 30° F. In other variations, the coolant may have a temperature between about 20° F. and about 25° F. In yet other variations, the coolant may have a temperature of about 23° F.

In other variations, the probe and/or cooling member may be cooled in other ways aside from continuously chilling and recirculating chilled coolant. In one variation, the cooling subsystem may simply chill the coolant to a sufficient level prior to use of the probe and/or cooling member on the patient, such that the coolant maintains its therapeutic cool temperature for a period sufficient to provide adequate cooling to the adipose tissue.

In another variation, the probe and/or cooling member may include a self-cooling material whose cooling may be "activated" prior to use on the patient. For example, the probe and/or cooling member may include a first compartment containing ammonium nitrate or calcium ammonium nitrate, and a second compartment containing water. The cooling of the probe and/or cooling member may be activated when the contents of the compartments are mixed (e.g., by breaking a separation between the compartments) to cause an endothermic reaction that cools the probe and/or cooling member. In other examples, the probe and/or cooling member may include compartments containing other substances that result in an endothermic reaction when combined.

Control Subsystem

In some variations, a control subsystem may be coupled to the cooling subsystem and control the flow rate and/or temperature of the coolant. A discussion of variations of a control subsystem for an internal probe is presented first and followed by control subsystem variations for an external cooling member.

Figure 11:
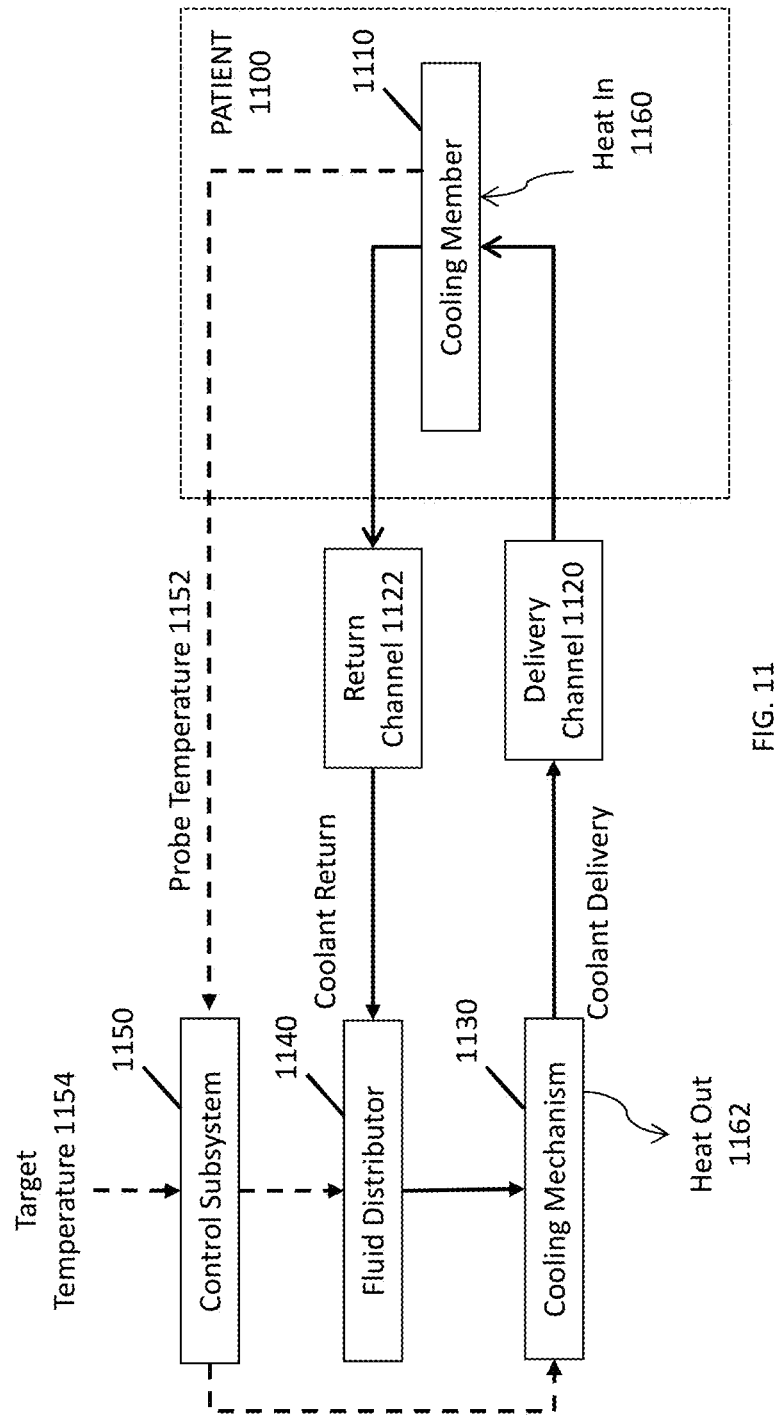
FIG. 11 depicts an illustrative block diagram of a control subsystem.

As shown in the block diagram of FIG. 11, in some variations, the control subsystem 1150 may be coupled to a fluid distributor 1140 (e.g., a pump) and/or a cooling mechanism 1130 (e.g., cooling reservoir or tank) of the cooling subsystem. The fluid distributor 1140 and cooling mechanism 1130 may cooperate to deliver a chilled coolant to the cooling member 1110 (e.g., probe). As the coolant circulates in the cooling member 1110 via delivery channel 1120 and return channel 1122, the cooling member 1110 and coolant absorb heat 1160 from and cools the targeted adipose tissue in the patient 1100. The coolant then returns from the cooling member 1110 to the cooling subsystem 1150 to be chilled and recirculated to the cooling member 1110.

Meanwhile, one or more temperature sensors in the cooling member 1110 may provide the cooling member temperature 1152 (e.g., the temperature of the adipose tissue interface surface) to the control subsystem 1150. Based on the measured temperature 1152 and a target temperature 1154 input, the control subsystem 1150 may control the fluid distributor 1140 to modulate the flow rate of the coolant and/or control the cooling mechanism 1130 to modulate the temperature or chilling rate of the coolant in the cooling subsystem. For example, the control subsystem 1150 may include a P, PI, or PID feedback controller to modulate the coolant flow rate in order to reach a target temperature 1154 for the adipose tissue interface surface of the cooling member 1110.

In some variations, the control subsystem 1150 modulates one or more parameters of the fluidic system to maintain turbulent flow of the coolant, which may help promote cooling of the adipose tissue surrounding the cooling member 1110. For example, the control subsystem may modulate flow rate of the coolant (given a particular lumen size, coolant viscosity, and other selected fixed parameters) to maintain a Reynolds number of at least approximately 4000. In some instances selection of a coolant with low viscosity and avoidance of large pressure gradients across the fluidic system may additionally or alternatively help the control subsystem maintain turbulent flow. In other variations, laminar flow of the coolant may be desirable.

Next, for variations of a cooling device comprising an external cooling member, a control subsystem 1750 as shown in FIG. 17 may be coupled to the cooling subsystem 1720 and may control the flow rate and/or temperature of the coolant 1722 in external cooling member 1710. The control subsystem 1750 may be similar to the control subsystem 1150 depicted in FIG. 11 and described in more detail above with respect to the system including an internal cooling device. In particular, the control subsystem 1750 may be coupled to a pump or other fluid distributor and/or a cooling mechanism 1730. The pump and cooling mechanism may cooperate to circulate a chilled coolant to and from the cooling member 1710. Meanwhile, one or more temperature sensors in the cooling member 1710 and/or securing member 1770 may provide temperature of the coolant, cooling member, and/or skin near the treatment region. Based on these measured temperatures and target temperature inputs, the control subsystem 1750 may modulate the flow rate of the coolant and/or chill temperature or chill rate of the coolant in the cooling subsystem. For example, the control subsystem 1750 may include a P, PI, or PID feedback controller to maintain target temperatures. Like the control subsystem 1150 described above, the control subsystem 1750 may modulate various parameters to maintain turbulent flow of the coolant in the cooling member 1710, but may alternatively modulate various parameters to maintain laminar flow.

Peripheral Components

In some variations, the system may include other peripheral components coupled to one or more of an internal probe and/or external cooling member that at least increase the effectiveness of cryolipolysis.

In some variations, the system may include other peripheral components described in detail below. In one variation, the system may include insulation at one or more locations along the pathway of the coolant, such as to maintain the temperature of the coolant as much as possible and to isolate the cooling effect to the selected portion of tissue overlying the target blood vessel. For instance, the portions of fluidic channel 1712 other than the treatment segments 1712a or 1712b may be insulated similar to that described below with reference to FIG. 16B. In another variation, the system may include one or more vasoconstrictors (e.g., described below in reference to FIGS. 12A-12D) that decrease perfusion of blood into the skin, thereby facilitating the cooling of adipose tissue underlying the skin. In another variation, the system may include mechanisms that hydrodissect and fracture adipose tissue (e.g., mechanisms described with reference to FIG. 13B), thereby increasing the thermal conductivity of the adipose tissue and facilitating the cooling of the affected adipose tissue. In another variation, the system may include an adipose tissue agitator that increases destruction of fat cell membranes (e.g., described with reference to FIG. 14, or a vibrating mechanism coupled to the cooling member or securing member), thereby increasing the thermal conductivity of the adipose tissue and facilitating the cooling of the affected adipose tissue.

Insulator

In some variations, the system may comprise insulation at one or more locations along the pathway of the coolant, which may help to spatially control the areas that are cooled. In particular, in some variations, as shown in FIG. 15A, the probe 1510 may comprise an insulator 1564 that extends axially along and at least partially circumferentially around the probe 1510. The insulator may extend along at least an axial portion of the treatment segment, or any suitable axial portion, of the probe 1510. Furthermore, the insulator 1564 may insulate only a circumferential portion of the probe 1510, such that the probe 1510 may cool tissue around only a portion of the circumference of the probe (e.g., a targeted region of adipose tissue of interest). For example, as shown in FIGS. 15A and 15B, the insulator 1564 may cover approximately 180 degrees of a hollow circular cylindrical probe 1510. In other variations, the insulator may cover a larger or smaller circumferential portion of the probe 1510 (e.g., about 80 degrees to about 300 degrees, about 120 degrees to about 260 degrees, about 160 degrees to about 220 degrees). As shown in FIG. 15A, in one variation, the probe 1510 of the cooling device 1502 may be inserted in adipose tissue directly below the skin 50, oriented such that at least a portion of the insulator 1564 is located between the probe 1510 and the skin 50. This orientation may direct the cooling away from the skin and/or help shield the skin from cold.

As shown in FIG. 15B, in another variation, the probe 1510 of the cooling device 1502 may be inserted in adipose tissue directly above the target vessel 60, oriented such that at least a portion of the insulator 1564 is located between the probe 1510 and the target vessel 60. This orientation may direct the cooling away from the target vessel 60 and/or help shield the target vessel 60 from cold. However, in other variations, the probe 1510 with insulator 1564 may be placed approximately halfway between the skin 50 and the target vessel 60, or at any suitable tissue depth and oriented with the insulator 1564 shielding or protecting any suitable region of tissue. In some variations, the insulator may include a material that is biostable and/or biocompatible, such as silicone rubber, or any other suitable material, that is coupled to the probe with an interference fit (e.g., an insulating sleeve slipped over the probe), epoxy, threads, or any suitable fastening means. In some variations, the insulator may additionally or alternatively be formed out of a thickened wall portion of the probe 1510.

In some variations, as shown in FIG. 16A, the probe 1610 may additionally or alternatively comprise an insulator 1664 that circumferentially surrounds at least a portion of the probe 1610 that is in contact with the skin 50 when the probe 1610 is inserted into the patient (i.e., a transcutaneous segment of the probe 1610). In this variation, the transcutaneous segment of the probe 1610 is insulated to help protect skin 50 from cold Like the insulators 1564 depicted in FIGS. 15A and 15B, the insulator 1664 may include a material that is biostable and/or biocompatible and coupled to the probe in the manner described above, and/or include a thickened wall portion of the probe 1610. Transmission lines 1656 (e.g., delivery channel, return channel) provide coolant to and/or from probe 1610.

In some variations, as shown in FIGS. 16A and 16B, the system may additionally or alternatively include an insulator 1666 in or around transmission lines 1656 delivering coolant to and/or from the probe 1610. The insulator 1666 may help maintain the temperature of the coolant passing through the transmission lines 1656. For example, the transmission lines 1666 passing between the cooling subsystem and the probe may include polyvinyl chloride tubing and foam rubber insulation. However, in other variations, the transmission lines 1656 and insulator 1666 may include any suitable material.

Vasoconstrictor

In some variations, the system may include a vasoconstrictor for decreasing perfusion of blood into the skin 50. Perfusion of blood into the skin may bring heat into the general treatment area of desired cooling, which may hamper or inhibit the desired outcome of adipose cell death. Vasoconstriction may decrease such perfusion and the amount of heat in the skin, thereby reducing interference with effective cooling of underlying adipose tissue. The vasoconstrictor may be coupled to at least one of the internal probe or external cooling members depending on the type of vasoconstrictor utilized.

Figure 12A:
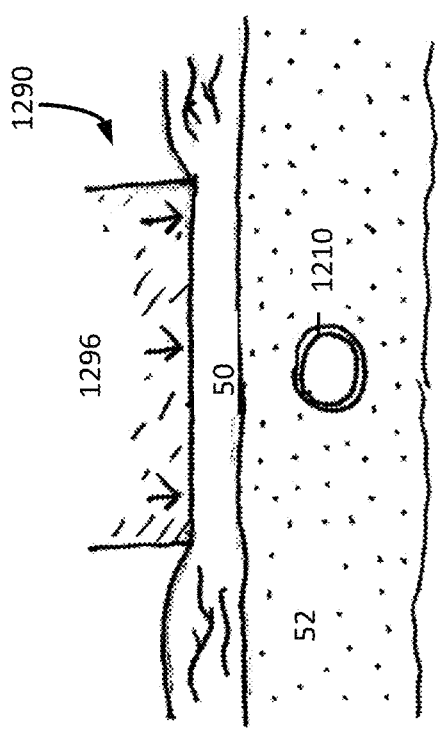
FIGS. 12A-12D depict variations of vasoconstrictors for vasoconstricting vasculature of the skin.

In some variations, as shown in FIG. 12A, the vasoconstrictor 1290 may be applied externally to the skin in order to cool the skin to a temperature cold enough to induce vasoconstriction, but not cold enough to cause cell death (e.g., between about 30° F. and about 35° F., or about 32° F.). For example, the vasoconstrictor may be a cold object 1292 placed adjacent to the skin 50, such as an ice pack or a highly thermally conductive metal like aluminum.

Figure 12B:
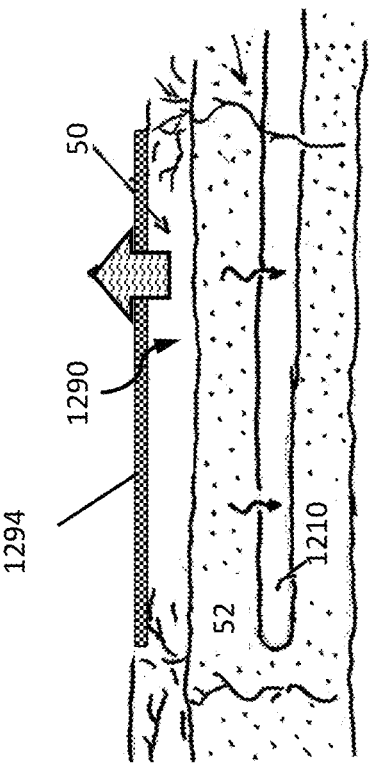

In some variations, positive or negative pressure is applied externally to the skin to cause vasoconstriction. As shown in FIG. 12B, the vasoconstrictor 1290 may include a source 1296 of positive pressure applied externally to the skin. For example, the vasoconstrictor 1290 may be a weight, or a cuff that is worn around the skin and is radially adjustable with elastic, drawstrings, hook and loop fastener, inflation, or other adjustable mechanisms.

Figure 12C:
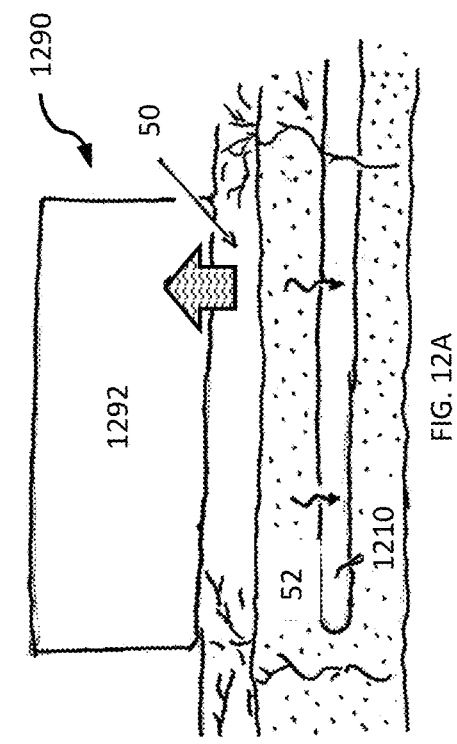

In some variations, as shown in FIG. 12C, the vasoconstrictor 1290 may include a source of negative pressure. For example, a suction cup 1298, cuff or other sealable item may be applied to the treatment site and attached to a vacuum. Reduction of pressure within the suction cup 1298 may compress vasculature in the skin at the boundary of the suction cup, thereby causing vasoconstriction of blood vessels supplying the skin 50 in the treatment area.

Figure 12D:
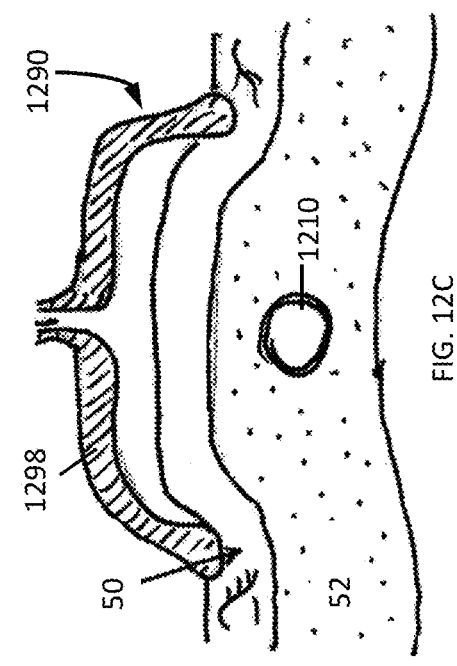

In yet other variations, as shown in FIG. 12D, the vasoconstriction may be caused by vasoconstrictive medication 1294, such as epinephrine cream, which is applied topically over the treatment site. Furthermore, the system may include any other suitable kinds of vasoconstrictors that reduce perfusion of blood into the skin. As shown in FIGS. 12A-12D, the vasoconstrictor may be operated while the probe 1210 cools the adipose tissue 52 underlying the skin 50, but in other variations, the vasoconstrictor may additionally and/or alternatively be operated prior to the insertion of the probe. In other variations, the system may include any suitable combination of vasoconstrictors.

Hydrodissector

In some variations, the system may include mechanisms that hydrodissect adipose tissue. Hydrodissection may be used to fracture the structure of the adipose tissue overlying the target vessel. Such fracturing may increase thermal conductivity of the adipose tissue such that the cooling probe has a greater therapeutic cooling reach, thereby allowing for reduction of a greater volume of adipose tissue. Hydrodissection may also involve the introduction of saline or another suitable fluid into the adipose tissue, where the fluid helps conduct cold within the adipose tissue.

In some variations, hydrodissection may be performed prior, or in close proximity, to insertion of a cooling probe (e.g., the probes described herein) and/or application of an external cooling member. In other variations, the hydrodissection may additionally or alternatively be performed simultaneously with the insertion of a cooling probe. Hydrodissection may be performed using a separate hydrodissection tool, or it may be performed using a cooling probe, such as the probes described herein, configured for hydrodissection. Depending on the length over the vessel that is hydrodissected, a volume of liquid between 1 cc and 20 cc may be used to hydrodissect adipose tissue with a near immediate effect.

In some variations, a target vessel is first located, such as via ultrasound, for insertion of a hydrodissection tool into adipose tissue above the target vessel. Fluid may then be injected to fragment adipose tissue. Thereafter, cryolipolysis treatment may be applied as discussed above.

In one example, as shown in FIG. 13A, the treatment segment of the probe 1310 inserted into adipose tissue 52 overlying the target vein 60 may include one or more fenestrations 1311 or pores that permit flow of saline or another suitable fluid from within the probe (e.g., a lumen for saline flow), through the adipose tissue interface surface of the probe, and into the surrounding adipose tissue 52. Thereafter, an internal and/or external cooling member may be applied to perform cryolipolysis as described above. In another example, as shown in FIG. 13B, hydrodissection may involve the injection of saline or another suitable fluid through the skin 50 into the adipose tissue 52 with a secondary instrument such as a syringe 1320. Thereafter, an internal and/or external cooling member may be applied to perform cryolipolysis as described above. In other variations, the system may include any suitable combination of mechanisms for hydrodissection.

Tissue Agitator

In some variations, the systems described herein may comprise a tissue agitator that agitates lipid crystals within fat cells in the adipose tissue, which may increase destruction of the fat cell membranes. Such destruction may enable the cooling probe to have a greater therapeutic effect, thereby allowing for reduction of a greater volume of adipose tissue. In some variations, the agitation may be performed using a cooling probe, such as the probes described herein. In other variations, the agitation may be performed by a separate tissue agitator. In some variations, the tissue agitator may be external to the patient. In one variation, a tissue agitator may be held to the surface of the skin either manually or using a strap and/or adhesive.

Similar to hydrodissection described above, tissue agitation may be performed prior to and/or simultaneously with insertion of a cooling probe into adipose tissue. In one variation, the lipids of the adipose tissue are crystalized before inducing vibration in the probe or application of an external tissue agitator on the surface of the skin. In some variations, agitation may be provide in a frequency range of 1 Hz to 300 Hz. However, tissue agitation may be provided during cooling treatment as well.

In one example, as shown in FIG. 14, the tissue agitator may include an external mechanical source of vibration such a vibrating motor 1462 (e.g., a brushed DC motor with an eccentric mass coupled to its shaft) that is applied adjacent to skin 50 above probe 1410 to vibrate underlying adipose tissue 52. In another example, the tissue agitator may be configured to be located within adipose tissue, such as a vibrator that is coupled to or incorporated into the probe, and/or a separate vibrating source such as a second probe that vibrates. In another example, the tissue agitator may comprise an external and/or internal source of acoustic vibration. In other variations, the system may comprise any suitable combination of tissue agitators.

Tissue Gatherer

Figure 20A:
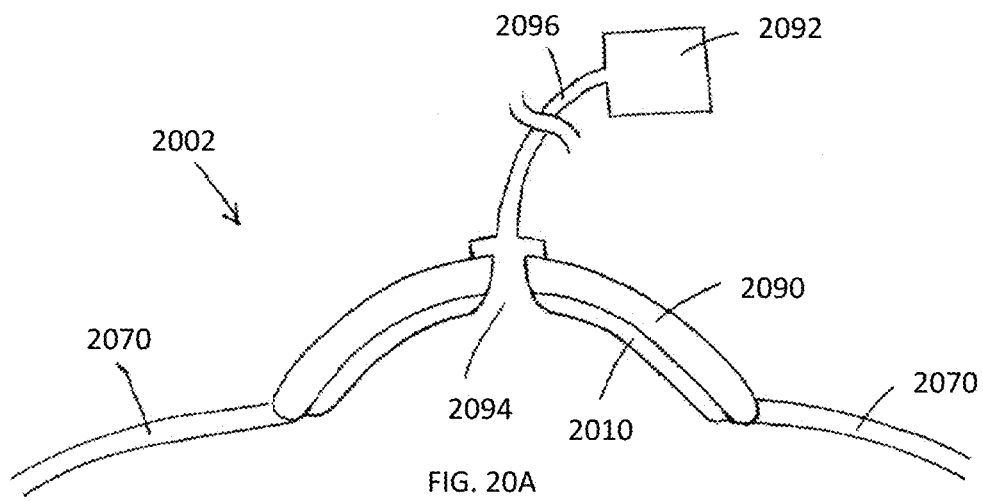
FIGS. 20A and 20B depict cross-sectional and perspective views, respectively, of a portion of a variation of a tissue gathering device.
Figure 20B:
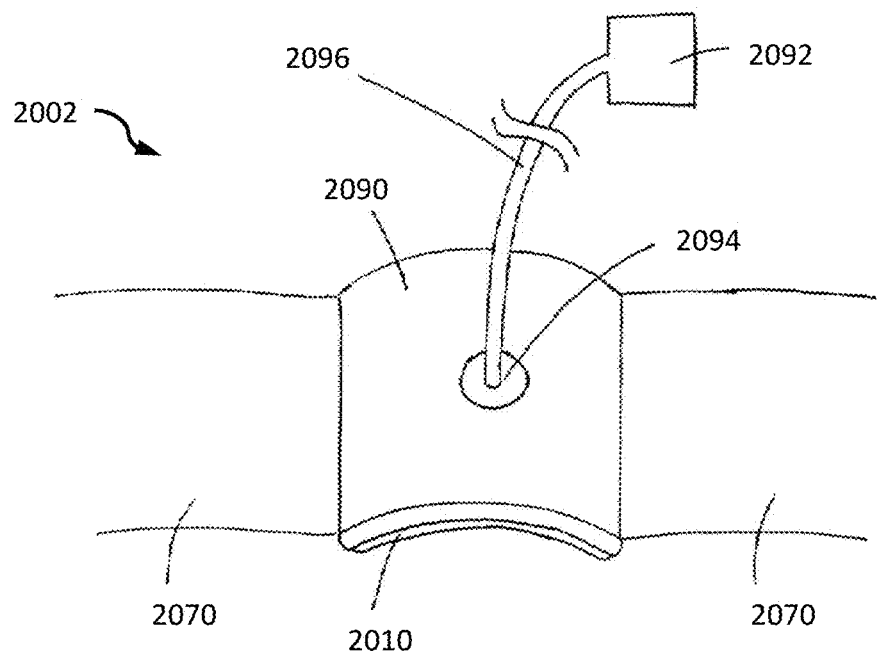

In some variations, the system may include a tissue gatherer device configured to gather one or more portions of patient tissue toward the cooling device. This may have benefits such as allowing the cooling device to make better contact with the tissue, or better isolating the cooling to the adipose tissue to be treated by the cooling device. In one variation, the system may gather patient tissue using negative pressure. FIGS. 20A and 20B show a cross-sectional view and a perspective view, respectively, of one variation of a cooling device 2002 configured to pull a one or more portions of the patient's tissue toward the cooling device 2002. The cooling device 2002 may include a tissue cup 2090, a cooling member 2010, a securing member 2070, and a vacuum source 2092. The tissue cup 2090 may have a concave shape to define a volume for holding tissue, and the cooling member 2010 may be located on an inner tissue interface surface of the tissue cup 2090. The volume defined by the tissue cup 2090 may be connected via a port 2094 and tubing 2096 to the vacuum source 2092. The tissue cup 2090 may be made of plastic or other suitable air-tight and/or insulating material. Securing member 2070 may be coupled to the tissue cup 2090 (e.g., with sutures or epoxy), and may be configured to secure the tissue cup 2090 to the patient such that cooling device 2010 is adjacent to the treatment area. When the vacuum source 2092 is activated, it may create a region of negative pressure within the tissue cup 2090, thereby pulling the tissue of the patient toward the tissue cup 2090 and against the cooling member 2010.

In some variations, the cooling device 2002 may include a single tissue cup 2090 and a single cooling member 2010. However, in other variations, the cooling device 2002 may include any suitable number of tissue cups and/or cooling members. For instance, the cooling device 2002 may include two tissue cups, each with a respective cooling member, where each tissue cup and cooling member combination may be configured to cool a region of tissue overlying a respective target blood vessel.

Figure 21A:
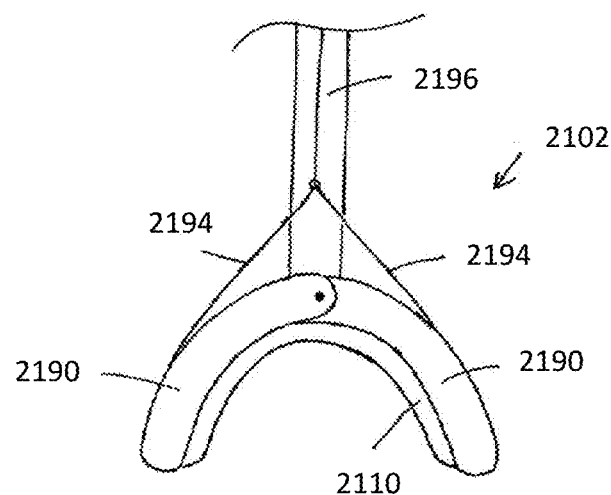
FIGS. 21A and 21B depict side and perspective views, respectively, of a portion of another variation of a tissue gathering device.
Figure 21B:
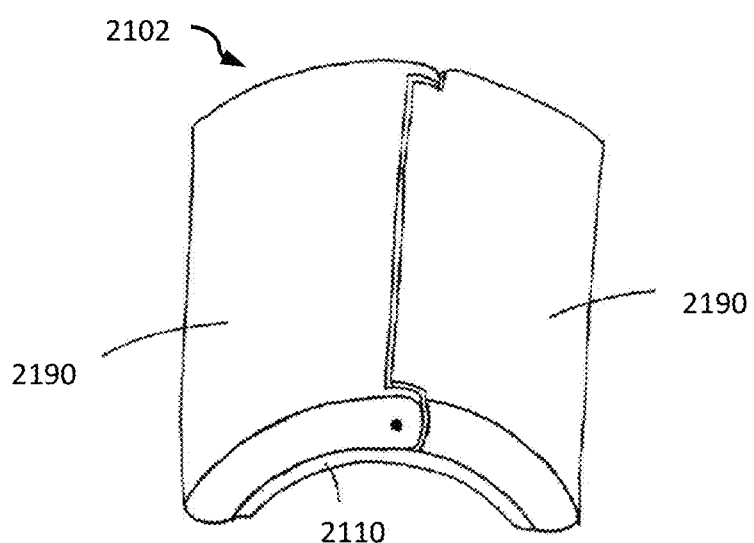

In another variation, the tissue gatherer may grasp the patient tissue. FIGS. 21A and 21B show a cross-sectional view and a perspective view, respectively, of another variation of a cooling device 2102 configured to pull one or more portions of patient tissue toward the cooling device 2102. In this variation, the cooling device 2102 may include a set of jaws 2190 and a cooling member 2110. The jaws may be made of a rigid plastic, or any other suitable rigid or semi-rigid material. The jaws 2190 may be movable between an open configuration and a closed configuration, such as by providing and releasing tension in pull wires 2194 using a handle 2196. However, any other suitable mechanism may actuate the jaws. In at least the closed configuration, the jaws 2190 may define a volume for holding tissue, and the cooling member 2110 may be located on an inner tissue interface surface of the jaws 2190. The jaws 2190 may be actuated to grasp a portion of patient tissue, which brings the tissue closer in contact with cooling member 2110.

Although FIGS. 21A and 21B depict a variation in which the set of jaws includes two jaws 2190, other variations may include three, four, or more than four jaws 2190. In some variations, the cooling device 2102 may include a single set of jaws 2190 and a single cooling member 2110, but in other variations, the cooling device 2102 may include any suitable number of sets of jaws and/or cooling members. For instance, the cooling device 2102 may include two sets of jaws, each with a respective cooling member, where each jaws and cooling member combination may be configured to cool a region of tissue overlying a respective target blood vessel.

Methods

Also described herein are methods of using the internal and external cooling devices described herein to cool adipose tissue overlying a treatment portion of a target blood vessel, which may cause a decrease in the thickness of the adipose tissue layer and improve percutaneous access to the target blood vessel. This effect of reduction of adipose tissue, as illustrated in FIG. 4, may occur gradually over a period of treatment or after treatment. In some variations, the method may be used to improve access to target blood vessels having fistulas, such as those used for facilitating dialysis. In these variations, the cooling treatment may be carried out after a fistula-formation procedure, or the cooling treatment may be carried out during (i.e., simultaneously with) or before a fistula-formation procedure. In yet other variations, the method may be used generally to improve access to any target blood vessel, regardless of whether the target vessel is involved in fistula formation.

Figure 23:
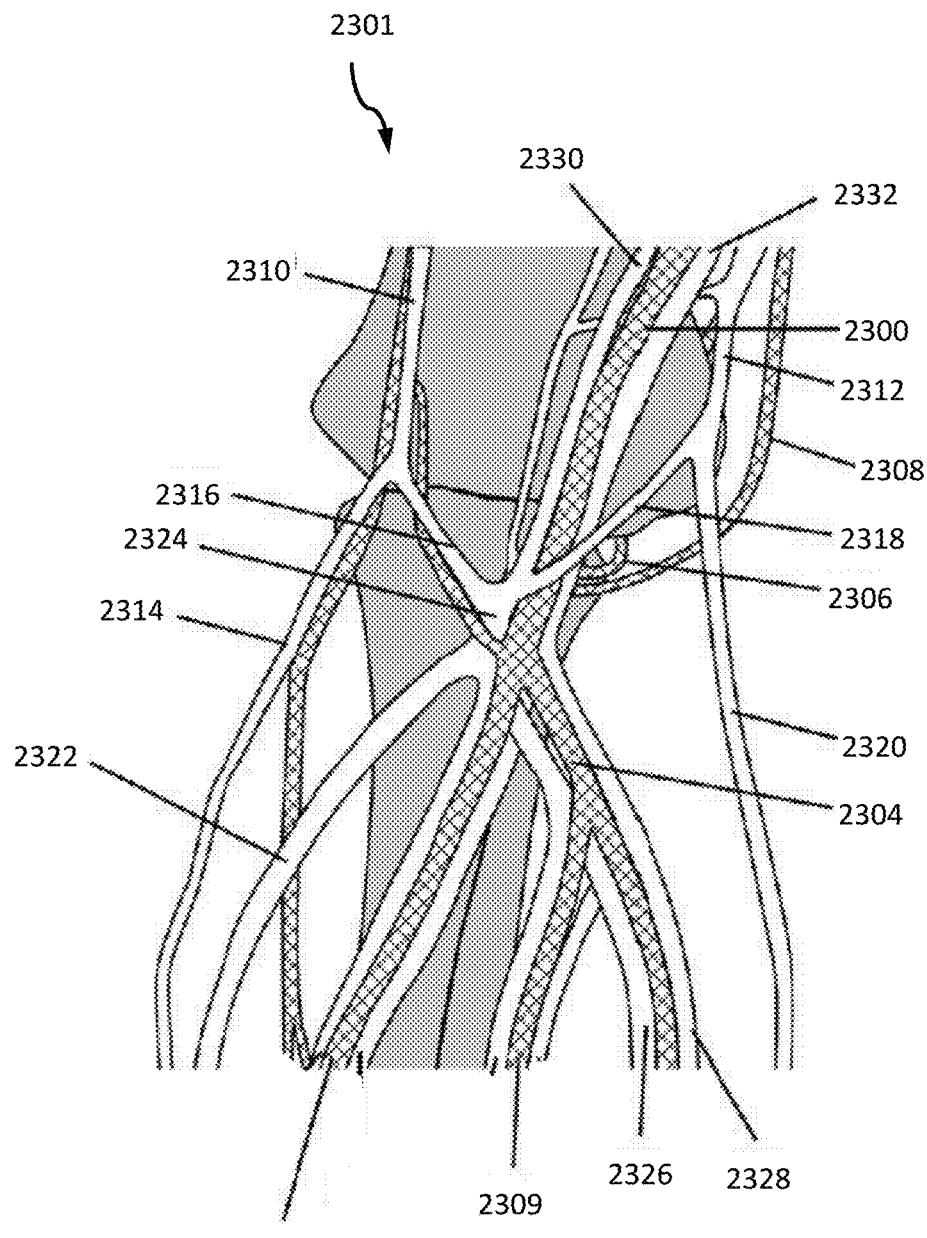
FIG. 23 is an illustrative depiction of at least a portion of the vascular anatomy of an arm of a human.

FIG. 23 shows a simplified depiction of the typical vascular anatomy of the arm around the elbow that may include one or more target blood vessels. Specifically, FIG. 23 shows an anterior view of the right arm 2301 as would be seen with the palm facing upward. As shown there, the brachial artery 2300 extends superficially and distally from the upper arm and sinks deeply into the arm near the elbow joint, where the brachial artery 2300 branches into the radial artery 2302 and the ulnar artery 2304. The upper portion of the ulnar artery 2304 is deeply seated within the arm beneath the superficial flexor muscles (not shown), and leads down the ulnar side of the forearm to the wrist. The anterior ulnar recurrent artery 2306 and the posterior ulnar recurrent artery 2308 branches off of the ulnar artery 2304 just below the elbow joint, and these arteries supply blood to the joint and surrounding muscles. Further down the arm, typically just below the radial tuberosity of the radius bone (not shown), the interosseous artery 2309 branches off from the ulnar artery 2304 and eventually feeds into the posterior and anterior interosseous arteries (not shown).

Also shown in FIG. 23 are the cephalic vein 2310/2314/2316 and the basilic vein 2312/2318/2320. The upper cephalic vein 2310 runs along the outer border of the bicep muscle (not shown) continues down into the forearm as lower cephalic vein 2314. The median cephalic vein 2316 joins the cephalic vein 2310/2314 near the elbow joint. The upper basilic vein 2312 runs along the inner side of the bicep muscle and continues into the forearm as basilic vein 2320). The lower basilic vein 2320 of the lower arm is sometimes referred to as the common ulnar vein. The median cubital vein 2318 (in some instances referred to as the median basilic vein) joins the upper basilic vein 2312 and the common ulnar vein 2320. The median cubital vein 2318 and the median cephalic vein 2316 are formed at the branching of the median antebrachial vein 2322. Near the branching of the median antebrachial vein 2322 into the median cubital vein 2318 and the medial cephalic vein 2316, a perforating branch 2324 connects these vessels with the deep veins of the arm through the antebrachial fascia (not shown).

As shown in FIG. 23, perforating branch 2324 communicates with a first deep ulnar vein 2326 and a second deep ulnar vein 2328. These deep ulnar veins 2326/2328 may run substantially parallel on either side of the ulnar artery 2304 between the brachial artery 2300 and the interosseous artery 2309, and may branch away from ulnar artery 2304 distal to the interosseous artery 2309. Between the brachial artery 2300 and the interosseous artery 2309, the deep ulnar veins 2326/2328 are typically located in close proximity to the ulnar artery 2304, and usually less than 2 mm separate the ulnar artery 2304 from the deep ulnar veins 2326/2328. Along the length of the deep ulnar veins 2326/2328, transverse branches (not shown) may occasionally connect to the deep ulnar veins 2326/2328. Also shown in FIG. 23 are first brachial vein 2330 and second brachial vein 2332. The brachial veins 2330/2332 generally run along the brachial artery 2300, and the deep ulnar veins 2326/2328 feed into the brachial veins 2330/2332 near the elbow joint. Additionally, a pair of radial veins (not shown) may run along the radial artery, and may feed into one or both of the brachial veins.

In some variations, the target blood vessel is a vessel accessed or intended to be accessed for dialysis purposes. Furthermore, the method may target multiple blood vessels simultaneously. For example, potential target blood vessels include the cephalic vein (e.g., a forearm segment or upper arm segment of the cephalic vein) and the basilic vein (e.g., a forearm segment or the median basilic vein segment near the elbow). The cephalic vein and basilic veins are common sites for arteriovenous fistulas that connect arterial flow to veins. However, the method may target other suitable portions of the cephalic vein, the basilic vein, and/or any other blood vessels whose access is obscured by adipose tissue. Vasculature in and around the treatment area of interest, including target blood vessels such as any veins that are arterialized through an arteriovenous fistula or any other suitable blood vessels, may be mapped using ultrasound or other suitable modalities prior to and/or during the treatment procedure.

In some variations, the methods of cryolipolysis described herein may be performed in particular with a surgical procedure to form a brachio-basilic fistula in order to provide a vein having sufficient blood flow necessary for dialysis, but which is otherwise obscured by a thick layer of adipose tissue. A method of facilitating percutaneous access to a target basilic vein in a patient may begin with applying local anesthesia, general anesthesia or a brachial plexus block to the arm of the patient. Next, a brachio-basilic fistula may be formed in the arm of the patient. The arm may be dissected to provide access to the adipose tissue overlying the target vein. A subcutaneous probe may then be inserted into adipose tissue overlying the target vein. After insertion, the probe may be aligned with a treatment portion of the target vein. The alignment of the probe may then be verified by either fluoroscopy or ultrasound. Additionally or alternatively, an external cooling member may be provided with a fluidic channel carrying a coolant substantially aligned with a treatment portion of the target vein. A securing member may be coupled to the cooling member to an external surface of the patient.

A selected portion of adipose tissue surrounding the probe may then be cooled, thereby forming a depression in the selected portion of adipose tissue overlying the treatment portion of the target vein. The probe and/or the external cooling member may be removed at the end of the cooling treatment period. After a sufficient recovery time has passed from the fistula and cryolipolysis procedures, hemodialysis treatment may be performed using the basilic vein.

After fistula formation, a recovery time on the order of several weeks or months is common for the fistula to mature. Similarly, the full effect of a cryolipolysis procedure may not be evident for about one to two months. Therefore, fistula formation and cryolipolysis may preferably be performed together or near in time to each other. In other variations, cryolipolysis may be performed before or after fistula formation.

Methods Using Internal Cooling

In some variations described here using internal cooling, the method of facilitating percutaneous access to a target blood vessel in a patient may include inserting a subcutaneous probe (or other elongate cooling member) into adipose tissue, aligning the probe with a treatment portion of the target blood vessel, and cooling a selected portion of adipose tissue surrounding the probe, thereby forming a depression in the selected portion of adipose tissue overlying the treatment portion of the target blood vessel. The depression may make the treatment portion of the target blood vessel closer to the surface of the skin, which may ease vascular access to that portion of the target blood vessel, since the target blood vessel is obscured by less fat. Accordingly, in some variations, the method may form a depression that is somewhat elongate and is approximately aligned with the treatment portion of the target blood vessel. In other variations, however, the depression may be a large general surface area (e.g., an approximate square, circle, or the like) that includes the area overlying the target blood vessel and more.

Inserting the probe into adipose tissue may comprise inserting a distal end of the probe into the adipose tissue at a first location. The first location may be proximate to (e.g., adjacent to, or otherwise nearby) a treatment portion of the target blood vessel. In some variations, as shown in FIG. 3A, the distal end of the probe remains in direct contact with the adipose tissue. In these variations, the distal end of the probe may include the treatment segment configured to cool surrounding adipose tissue. In other variations, as shown in FIG. 3B, the distal end of the probe is passed out of the adipose tissue at a second location different from the first location. In the variation shown in FIG. 3B, the distal end of the probe may lie external to the patient, while a more proximal segment of the probe includes the treatment segment configured to cool surrounding adipose tissue. Furthermore, in some variations of the method, multiple probes may be inserted proximate one or more target blood vessels. For example, multiple probes may be inserted in parallel to simultaneously improve access to multiple target blood vessels. As another example, multiple probes may be placed in series in a path approximately tracking the shape of the target blood vessel, such as to improve access to a curved target blood vessel. The one or more probes may include any of the various probes described above, such as that of FIGS. 3-9, but may additionally or alternatively include any suitable cooling members.

In some variations, the patient skin at the first insertion point (the location where the distal end of the probe is inserted) may be punctured separately prior to inserting the probe. In these variations, the distal end of the probe may be blunt to help avoid any undesired trauma to the blood vessel or other tissue. For example, the skin may be punctured by a needle, or an incision may be formed to that enable the probe to enter the adipose tissue. As another example, the skin may be punctured by a trocar or other cannula through which the probe may subsequently enter the adipose tissue. However, in other variations, the probe may puncture the skin directly. For example, the probe may include a distal sharpened end (e.g., a blade) that may or may not be removed from the probe after the distal end of the probe is initially inserted into the adipose tissue.

Aligning the probe with a treatment portion of the target blood vessel may include tracking, within the adipose tissue, the path of at least the treatment portion of the target blood vessel. As shown in FIG. 3A, the treatment portion 310a of the probe may be approximately parallel to the treatment portion of the target blood vessel 60. Depending on factors such as the size and cooling range of the probe, the probe may be aligned with the vessel at various depths within the adipose tissue. In one example, the treatment portion of the probe may be aligned with the blood vessel at a depth approximately halfway between the skin and the blood vessel. However, the probe may be located below the skin at approximately one-third of the distance between the skin and the blood vessel, approximately two-thirds of the distance between the skin and the blood vessel, or at any suitable depth.

In some variations, aligning the probe may include guiding the depth of the probe and/or otherwise orienting the probe. Guiding the depth of the probe may be performed with the aid of a guide member, such as a magnetic guide member that is external to the patient or internal to the target blood vessel and magnetically attracts and/or repels at least a portion of the probe to adjust the depth of the probe in the adipose tissue. Orienting the probe may include adjusting the probe such that an insulator coupled to the probe is facing any tissue to be protected. In some variations, viewing radiopaque markers or other markings on the probe under fluoroscopy or other imaging modalities may help align and/or orient the probe in the adipose tissue. Additionally or alternatively, probe alignment may be aided with other imaging modalities to image the probe and/or the target vessel, such as near-infrared light.

Cooling a selected portion of adipose tissue surrounding the probe may comprise cooling the probe. In a first variation, cooling the probe may comprise circulating a coolant in the probe. In some variations, cooling the probe may include inducing turbulent flow of the coolant. As described above with reference to internal cooling devices, the circulated coolant may be a fluid such as liquid or gas. The circulated coolant may be repeatedly chilled and delivered to the probe from a cooling subsystem, or may originate from a chilled coolant reservoir coupled to the probe. A control subsystem may control the flow rate and/or temperature of the coolant based on the comparison between a measured probe or coolant temperature and a target probe or coolant temperature. In some variations, as described above, circulating a coolant in the probe may comprise allowing phase changes in the coolant upon absorbing heat from the surrounding region of adipose tissue (e.g., allowing liquid coolant to vaporize). After having undergone a phase change, the warmed coolant may return to a cooling subsystem or be vented outside the probe. In a second variation, cooling the probe may comprise providing a coolant insert in the form of a solid or semi-solid coolant in the probe.

Cooling the adipose tissue may be performed in a single session or repeated in multiple sessions over a treatment period of time. Generally, during each session, the tissue may be cooled for between about 1 minute and about 2 hours. In some variations, in each session the tissue may be cooled for between about 1 hour and about 2 hours. In some variations, in each session the tissue may be cooled for between about 1 minute and about 30 minutes. In some variations, in each session the tissue may be cooled for between about 1 hour and about 1.5 hours. In some variations, in each session the tissue may be cooled for between about 1.5 hours and about 2 hours. In some variations, in each session the tissue may be cooled for between about 10 minutes and about 20 minutes. In some variations, the cooling time for each session may be chosen based on the thickness of the adipose tissue between the skin and the target vessel. During a treatment session, in some variations all or a portion of the tissue may be cooled to a temperature between about 0° F. and about 40° F. In some variations, all or a portion of the tissue may be cooled to a temperature between about 5° F. and about 25° F. In some variations, all or a portion of the tissue may be cooled to a temperature between about 20° F. and about 25° F. In some variations, all or a portion of the tissue may be cooled to a temperature between about 20° F. and about 30° F. Generally, the frequency of the session and the duration of the treatment period may depend on the rate of tissue reduction in response to cumulative treatment sessions and/or may depend on the dimensions of the desired depression or "trench" over the treatment portion of the target blood vessel. However, generally speaking, the treatment period may be between approximately 1 week to approximately 8 weeks, or approximately 3 weeks to approximately 6 weeks. In some variations, the tissue may be treated in a single treatment session. In some variations, cooling the selected portion of adipose tissue may allow the skin overlying the depression to lie within about 7 millimeters of the treatment portion of the target blood vessel (i.e., the thickness of the layer of adipose tissue between the skin and the treatment portion of the target blood vessel may be reduced to less than or about 7 millimeters). In some variations, cooling the selected portion of adipose tissue may allow the skin overlying the depression to lie within about 5 millimeters of the treatment portion of the target blood vessel (i.e., the thickness of the layer of adipose tissue between the skin and the treatment portion of the target blood vessel may be reduced to less than or about 5 millimeters thick). In some variations, this adipose tissue layer thickness may correspond to a desired depth of the depression between about 10 millimeters and about 40 millimeters deep, such as about 25 millimeters deep. In some variations, the depression may be elongate and track the shape of the treatment portion of the underlying target blood vessel. For example, in these variations, the depression may be between about 80 millimeters and 120 millimeters long, such as about 100 millimeters long.

In one variation, method of treatment of a patient undergoing a brachio-basilic fistula procedure and cryolipolysis procedure begins with a determination of the location of a basilic vein. A subcutaneous blunt dissection may then be performed with a surgical tool such as a trocar to access the area of adipose tissue overlying a target basilic vein. A cooling member is then inserted into the adipose tissue. The position and location of the inserted cooling member may be verified by, for example, fluoroscopy or ultrasound. For adipose tissue having a depth of 16 mm between the skin and the target blood vessel, the dissection may be performed to insert a cooling member at a depth of 8 mm from the skin surface. The cooling member may define a blunt distal portion and have a diameter of 5 mm. The cooling member is cooled for 30 minutes at a temperature of 30° F. The above-described process may be performed under local or general anesthesia, or a brachial plexus block.

Once cryolipolysis treatment is completed, the cooling member is removed, and the cooling member incision is closed. Thereafter, a procedure may be performed to form a brachio-basilic fistula. Once the fistula has matured and the targeted area of adipose tissue has receded, access to a target blood vessel is improved, leading to better outcomes for hemodialysis treatment. Cryolipolysis treatment is not dependent on a particular procedure such as a brachio-basilic fistula procedure and may be performed separately or in conjunction with other procedures on other target blood vessels.

In some variations, the method may comprise vasoconstricting vasculature in the skin of the patient overlying the selected portion of adipose tissue and the treatment portion of the target blood vessel. Vasoconstricting the skin vasculature may be performed prior to or simultaneously with the process of cooling the adipose tissue. In one example, vasoconstricting may comprise applying cold therapy to the external surface of the skin, such as placing on the skin a cold object (e.g., ice pack or highly thermally conductive metal) that has a temperature cold enough to induce vasoconstriction, but not cold enough to cause necrosis. In another example, vasoconstricting may comprise applying a source of positive pressure (e.g., radial compression or a weight) onto the skin. In another example, vasoconstricting may comprise applying a source of negative pressure (e.g., suction cup with vacuum) onto the skin. In yet another example, vasoconstricting may comprise applying a vasoconstricting substance, such as epinephrine cream, to the skin. Vasoconstricting may involve any suitable combination of vasoconstricting processes.

In some variations, the method further includes hydrodissecting the selected portion of adipose tissue overlying the treatment portion of the target blood vessel. Hydrodissecting may be performed prior to or simultaneously with the process of cooling the adipose tissue. In one example, hydrodissecting may include injecting saline or another suitable fluid into the adipose tissue percutaneously. In another example, hydrodissecting may include introducing saline or another suitable fluid through the probe (e.g., through fenestrations in the treatment segment of the probe). Hydrodissecting the tissue may involve any suitable combination of hydrodissecting processes.

In some variations, the method may comprise agitating the selected portion of adipose tissue overlying the treatment portion of the target blood vessel. The agitation may be performed prior to or simultaneously with the process of cooling the adipose tissue. The agitation may be a mechanical vibration, such an external source (e.g. a vibrating motor placed on the skin adjacent the adipose tissue to be agitated) or an internal source (e.g., a vibrating probe). As another example, agitation may be generated by an external or internal source of acoustic vibration. Tissue agitation may involve any suitable combination of agitation processes.

Methods Using External Cooling

In some variations of methods using external cooling, the method of facilitating percutaneous access to a target blood vessel in a patient includes providing a cooling member including an elongate fluidic channel, aligning the fluidic channel with a treatment portion of the target blood vessel, coupling the cooling member to an external surface of the patient, and cooling a selected portion of adipose tissue overlying the treatment portion of the target blood vessel, thereby forming a depression in the selected portion of tissue. Similar to the depressions formed by methods using internal cooling, the depression formed by external cooling may make the treatment portion of the target blood vessel closer to the surface of the skin, which may ease vascular access to that portion of the target blood vessel, since the target blood vessel is obscured by less fat. Accordingly, in some variations, the method may form a depression that is somewhat elongate and is approximately aligned with the treatment portion of the target blood vessel. In other variations, however, the depression may be a large general surface area (e.g., an approximate square, circle, or the like) that includes the area overlying the target blood vessel.

The provided cooling member may be similar to those described above with respect to external cooling devices, or may be any suitable cooling member with a fluidic channel. The cooling member may be attached to the patient using a securing member (e.g., cuff). In variations in which the cooling member configuration is adjustable relative to the securing member, the cooling member may be adjusted to align with or track the target vessel before the securing member couples the cooling member to the patient. Alternatively or additionally, such adjustment in alignment may be performed while the securing member couples the cooling member to the patient, and/or after the securing member couples the cooling member to the patient. In variations in which the securing member is configured to have variable compressive force, the compressive force on all or a portion of the cooling member may be adjusted before, during, or after attachment of the cooling member to the patient.

As in the method of using internal cooling, cooling the adipose tissue with an external cooling device may be performed in a single session or repeated in multiple sessions over a treatment period of time. In some variations, the cooling time for each session may be chosen based on the thickness of the adipose tissue between the skin and the target vessel. Furthermore, generally, the frequency of the session and the duration of the treatment period may depend on the rate of tissue reduction in response to cumulative treatment sessions and/or may depend on the dimensions of the desired depression or "trench" over the treatment portion of the target blood vessel. Other aspects of the frequency and duration of cooling treatment sessions and treatment period are described in further detail above with respect to methods using internal cooling.

In some variations, the method may comprise vasoconstricting skin vasculature, hydrodissecting adipose tissue overlying the treatment portion of the target blood vessel, and/or agitating the adipose tissue overlying the treatment portion of the target blood vessel. These vasoconstricting, hydrodissecting, and tissue agitating processes may be similar to those described above with respect to methods using internal cooling.

It will be understood that the foregoing is only illustrative of the principles of the invention, and that various modifications, alterations, and combinations may be made by those skilled in the art without departing from the scope and spirit of the invention. Accordingly, the variations of the devices, systems, and methods for internal and external cooling of adipose tissue can be combined and/or permutated in any suitable manner.

The invention claimed is:

1. A method of facilitating percutaneous access to a target blood vessel in a patient, comprising:
   determining a path of at least a treatment portion of the target blood vessel;
   inserting a subcutaneous probe into adipose tissue;
   aligning the probe with the treatment portion of the target blood vessel; and
   cooling a selected portion of adipose tissue surrounding the probe, thereby forming a depression in the selected portion of adipose tissue overlying the treatment portion of the target blood vessel.

2. The method of claim 1, wherein inserting the probe comprises inserting a distal end of the probe into the adipose tissue at a first location proximate the treatment portion of the target blood vessel.

3. The method of claim 2, wherein inserting the probe further comprises passing the distal end of the probe out of the adipose tissue at a second location different from the first location.

4. The method of claim 1, wherein cooling the selected portion of adipose tissue comprises circulating a coolant in the probe.

5. The method of claim 4, further comprising measuring a temperature of the probe and modulating at least one of a flow rate and a temperature of the coolant based on the measured temperature of the probe.

6. The method of claim 4, wherein circulating the coolant in the probe comprises allowing the coolant to absorb heat from the selected portion of the adipose tissue and vaporize from a liquid coolant into a gaseous coolant.

7. The method of claim 6, wherein circulating the coolant in the probe comprises allowing the gaseous coolant to enter a return lumen of the probe.

8. The method of claim 1, wherein cooling the selected portion of the adipose tissue comprises providing a solid or semi-solid coolant into the probe and allowing the solid or semi-solid coolant to undergo a phase transformation into a liquid or gas upon absorbing heat from the selected portion of the adipose tissue.

9. The method of claim 1, further comprising vasoconstricting vasculature in a skin of the patient overlying the selected portion of the adipose tissue.

10. The method of claim 9, wherein vasoconstricting vasculature comprises applying cold therapy to the skin of the patient overlying the selected portion of the adipose tissue.

11. The method of claim 9, wherein vasoconstricting vasculature comprises applying a vasoconstricting substance to the skin of the patient overlying the selected portion of the adipose tissue.

12. The method of claim 9, wherein vasoconstricting vasculature comprises applying positive pressure to the skin of the patient overlying the selected portion of the adipose tissue.

13. The method of claim 9, wherein vasoconstricting vasculature comprises applying negative pressure to the skin of the patient overlying the selected portion of the adipose tissue.

* * * * *

UNITED STATES PATENT AND TRADEMARK OFFICE
CERTIFICATE OF CORRECTION

PATENT NO. : 10,646,666 B2
APPLICATION NO. : 14/838225
DATED : May 12, 2020
INVENTOR(S) : William E. Cohn, Thomas Diffley Pate and Adam L. Berman Page 1 of 1

It is certified that error appears in the above-identified patent and that said Letters Patent is hereby corrected as shown below:

On the Title Page

In page 2, Column 2, item (56), U.S. patent documents, Line no. 10, delete "Marion" and insert --Marion et al.--, therefor.

In page 2, Column 2, item (56), U.S. patent documents, Line no. 41, delete "Hassell et al." and insert --Hassett et al.--, therefor.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*